US008084249B2

(12) United States Patent
Kingsman et al.

(10) Patent No.: US 8,084,249 B2
(45) **Date of Patent: *Dec. 27, 2011**

(54) VECTOR

(75) Inventors: Susan Mary Kingsman, Oxford (GB); Christopher Robert Bebbington, San Mateo, CA (US); Fiona Margaret Ellard, Oxford (GB); Miles William Carroll, Oxon (GB); Kevin Alan Myers, Oxford (GB)

(73) Assignee: Oxford Biomedica (UK) Limited, Oxford (GB)

(*) Notice: Subject to any disclaimer, the term of this patent is extended or adjusted under 35 U.S.C. 154(b) by 0 days.

This patent is subject to a terminal disclaimer.

(21) Appl. No.: 12/714,264

(22) Filed: Feb. 26, 2010

(65) Prior Publication Data

US 2011/0065173 A1 Mar. 17, 2011

Related U.S. Application Data

(60) Continuation of application No. 11/380,188, filed on Apr. 25, 2006, now Pat. No. 7,718,627, which is a continuation of application No. 10/104,522, filed on Mar. 22, 2002, now Pat. No. 7,531,648, which is a division of application No. 09/445,375, filed as application No. PCT/GB98/01627 on Jun. 4, 1998, now Pat. No. 6,852,703.

(30) Foreign Application Priority Data

| | | |
|---|---|---|
| Jun. 4, 1997 | (GB) | 9711579.4 |
| Jun. 20, 1997 | (GB) | 9713150.2 |
| Jul. 4, 1997 | (GB) | 9714230.1 |

(51) Int. Cl.
*C12N 15/00* (2006.01)

(52) U.S. Cl. .................................................. 435/320.1

(58) Field of Classification Search ................ 435/320.1
See application file for complete search history.

(56) References Cited

U.S. PATENT DOCUMENTS

| | | | |
|---|---|---|---|
| 4,997,913 | A | 3/1991 | Hallstrom et al. |
| 5,559,099 | A | 9/1996 | Wickham et al. |
| 5,591,624 | A | 1/1997 | Barber et al. |
| 5,824,782 | A | 10/1998 | Holzer et al. |
| 5,856,140 | A | 1/1999 | Chimamura et al. |
| 5,876,691 | A | 3/1999 | Chester et al. |
| 6,143,520 | A | 11/2000 | Marasco et al. |
| 6,277,972 | B1 | 8/2001 | Afar et al. |
| 6,348,584 | B1 | 2/2002 | Hodgson et al. |
| 6,514,498 | B1 | 2/2003 | Antonsson et al. |
| 6,852,703 | B1 | 2/2005 | Kingsman et al. |
| 7,074,909 | B2 | 7/2006 | Kingsman et al. |
| 2007/0161080 | A1 | 7/2007 | Kingsman et al. |

FOREIGN PATENT DOCUMENTS

| | | | |
|---|---|---|---|
| EP | 0 336 562 | A1 | 10/1989 |
| EP | 0803574 | A2 | 10/1997 |
| WO | WO-89/07947 | A1 | 9/1989 |
| WO | WO-96/30504 | A1 | 5/1990 |
| WO | WO-92/11383 | A1 | 7/1992 |
| WO | WO-92/22653 | A1 | 12/1992 |
| WO | WO-94/11513 | A1 | 5/1994 |
| WO | WO-96/15238 | A1 | 5/1996 |
| WO | WO-96/30512 | A1 | 10/1996 |
| WO | WO-96/34969 | A2 | 11/1996 |
| WO | WO-97/17090 | | 5/1997 |
| WO | WO-97/36932 | A1 | 10/1997 |
| WO | WO-98/55607 | A2 | 12/1998 |
| WO | WO-01/36486 | A2 | 5/2001 |

OTHER PUBLICATIONS

Alvarez et al., "A Phase I Study of Recombinant Adenovirus Vector-Mediated Delivery of an Anti-erbB-2 Single-Chain (sFv) Antibody Gene for Previously Treated Ovarian and Extraovarian Cancer Patients," *Human Gene Therapy,* 8:229-242 (1997).
Anderson, F.W., "Human gene therapy," Nature, 392:25-30 (1998).
Arafat et al., "Effective single chain antibody (scFv) concentrations in vivo via adenoviral vector mediated expression of secretory scFv," *Gene Therapy,* 9:256-262 (2002).
Cameron, E., "Recent Advances in Transgenic Technology," Mol. Bio., 7:253-265 (1997).
Chamberlain et al., "Costimmulation Enhances the Active Immunotherapy Effect of Recombinant Anticancer Vaccines," Cancer Research, 56:2832-2836 (1996).
Chaudhary et al., "A rapid method of cloning functional variable-region antibody genes in *Escherichia coli* as single-chain immunotoxins," PNAS, 87:1066-1070 (1990).
Crystal, R., "Transfer of Genes to Humans: Early Lessons and Obstacles to Success," Science, 270:404-410 (1995).
Deshane et al., "Targeted Tumor Killing via an Intracellular Antibody against erbB-2," *J. Clin. Invest.,* 96:2980-2989 (1995).
European Search Report for 05 02 5532, dated Jul. 10, 2006.
Forsberg et al., "Identification of Framework Residues in a Secreted Recombinant Antibody Fragment that Control Production Level and Localization in *Escherichia coli,*" The Jour. of Bio. Chem., 272(19):12430-12436 (1997).
Gerstmayer et al., "Costimulation of T Cell Proliferation by a Chimeric B7-2 Antibody Fusion Protein Specifically Targeted to Cells Expression the erbB2 Proto-Oncogene," *Jour. of Immun.,* 158:4584-4590 (1997).
Greco et al., "Cancer Gene Therapy: delivery, delivery, delivery," Frontiers in Bioscience, 7:1516-1524 (2002). Hammer et al., "Spontaneous Inflammatory Disease in Transgenic Rats Expressing HLA-B27 and Human $\beta_2$m: An Animal Model of HLA-B27-Associated Human Disorders," Cell, 63:1099-1112 (1990).
Houdebine, L., "Production of pharmaceutical proteins from transgenic animals," J. Biotech, 34:269-287 (1994).
Jannot et al., "Intracellular expression of a single-chain antibody directed to the EGFR leads to growth inhibition of tumor cells," *Oncogene,* 13:275-282 (1996).
Kappel et al., "Regulating gene expression in transgenic animals," Current Opinions in Biotechnology, 3:548-553 (1992).

(Continued)

*Primary Examiner* — J. E. Angell

(74) *Attorney, Agent, or Firm* — Marshall, Gerstein & Borun LLP

(57) ABSTRACT

A vector comprising a nucleotide sequence of interest ("NOI") encoding a product of interest ("POI") is described. The NOI and/or the POI is capable of recognizing a tumor, such that in use the vector is capable of delivering the NOI and/or the POI to the tumor.

6 Claims, 11 Drawing Sheets

OTHER PUBLICATIONS

Figure 3A:
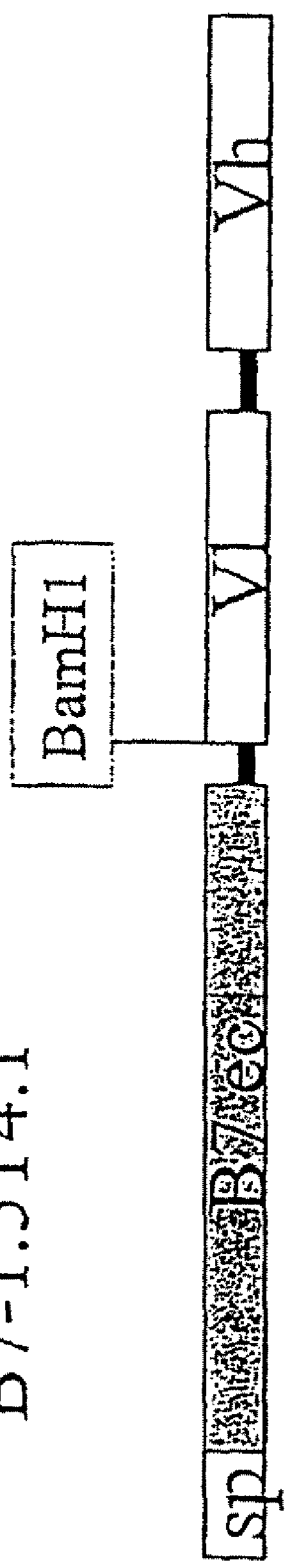

Lamikanra et al., "In vivo evaluation of an EIAV vector for the systemic genetic delivery of therapeutic antibodies," *Gene Therapy*, 12:988-998 (2005).
Leong et al., "Transfection of the gene for B7-1 but not B7-2 can induce immunity to murine malignant mesothelioma," Int. J. Cancer, 71:476-82 (1997).
Mountain, A., "Gene therapy: the first decade," TIBTECH, 18:119-127 (2000).
Mullins et al., "Expression of the DBA/2J Ren-2 gene in the adrenal gland of transgenic mice," EMBO Journal, 8(13):4065-4072 (1989).
Mullins et al., "Fulminant hypertension in transgenic rats harbouring the mouse Ren-2 gene," Nature, 344:541-544 (1990).
Mullins et al., "Transgenesis in Nonmurine Species," Hypertension, 22:630-633 (1993).
Mullins et al., "Transgenesis in the Rat and Larger Mammals," J. Clin. Invest., 98:S37-S40 (1996).
Myers et al., "Isolation of a cDNA Encoding 5T4 Oncofetal Trophoblast Glycoprotein," Jour. of Bio. Chem., 269(12):9319-9324 (1994).
Myers et al., Targeting immune effector molecules to human tumor cells through genetic delivery of 5T4-specific scFv fusion proteins, *Cancer Gene Therapy*, 9:884-896 (2002).
Naldini et al., "In vivo gene delivery and stable transduction of nondividing cells by a lentiviral vector," Science, 272:263-267 (1996).
Niemann, H., "Transgenic farm animals get off the ground," Transgenic Research, 7:73-75 (1998).
Osaki et al., "Gene Therapy for Carcinoembryonic Antigen-producing Human Lung Cancer Cells by Cell Type-specific Expression of Herpes Simplex Virus Thymidine Kinase Gene," Cancer Research, 54:5258-5261 (1994).
Overbeek, P., "Factors affecting transgenic animal production," Transgenic Animal Technology, 96-98 (1994).
Promega, Catalog of Nucleic Acids, pp. 215-216 (1993/94).
Richter et al., "Clinical gene therapy in hematology: Past and future," Int. Jour. Hematology, 73:162-169 (2001).
Riddell et al., "T-cell mediated rejection of gene-modified HIV-specific cytotoxic T lymphocytes in HIV-infected patients," Nature Medicine, 2:216-221 (1996).
Rieger et al., Glossary of Genetics and Cytogenetics, Classical and Molecular, 4th Ed., Springer-Verlag, Berlin (1976).
Rudikoff et al., "Single amino acid substitution altering antigen-binding specificity," Proc. Natl. Acad. Sci. USA, 79:1979-1983 (1982).
Scherf et al., "Cytotoxic and Antitumor Activity of a Recombinant Tumor Necrosis Factor-B1(Fv) Fusion Protein on $Le^{Y}$ Antigen-expressing Human Cancer Cells," *Clin. Cancer Res.*, 2:1523-1531 (1996).
Taurog et al., "HLA-B27 in Inbred and Non-Inbred Transgenic Mice," Jour. of Immun., 141(11):4020-4023 (1988).
Verma et al., "Gene therapy promises, problems and prospects," Nature, 389:239-242 (1997).
Wall, R.J., "Transgenic Livestock: Progress and Prospects for the Future," Theriogenology, 45:57-68 (1996).
Walter et al., "Viral Vectors for Gene Transfer," Drugs, 2:249-271 (2000).
Wels et al., "Biotechnological and gene therapeutic strategies in cancer treatment," *Gene*, 159:73-80 (1995).
Xiang et al., "Genetic engineering of a recombinant fusion possessing anti-tumor $F(ab')_2$ and tumor necrosis factor," *Jour. of Bio.*, 53:3-12 (1997).

Figure 1A SEQ ID No 1.

```
1     GAGGTCCAGC TTCAGCAGTC TGGACCTGAC CTGGTGAAGC CTGGGGCTTC
       E  V  Q   L  Q  Q  S   G  P  D   L  V  K   P  G  A  S

51    AGTGAAGATA TCCTGCAAGG CTTCTGGTTA CTCATTCACT GGCTACTACA
        V  K  I   S  C  K   A  S  G  Y   S  F  T   G  Y  Y

101   TGCACTGGGT GAAGCAGAGC CATGGAAAGA GCCTTGAGTG GATTGGACGT
      M  H  W  V   K  Q  S   H  G  K   S  L  E  W   I  G  R

151   ATTAATCCTA ACAATGGTGT TACTCTCTAC AACCAGAAAT TCAAGGACAA
       I  N  P   N  N  G  V   T  L  Y   N  Q  K   F  K  D  K

201   GGCCATATTA ACTGTAGACA AGTCATCCAC CACAGCCTAC ATGGAGCTCC
        A  I  L   T  V  D   K  S  S  T   T  A  Y   M  E  L

251   GCAGCCTGAC ATCTGAGGAC TCTGCGGTCT ATTACTGTGC AAGATCTACT
      R  S  L  T   S  E  D   S  A  V   Y  Y  C  A   R  S  T

301   ATGATTACGA ACTATGTTAT GGACTACTGG GGTCAAGTAA CCTCAGTCAC
       M  I  T   N  Y  V  M   D  Y  W   G  Q  V   T  S  V  T

351   CGTCTCCTCA GGTGGTGGTG GGAGCGGTGG TGGCGGCACT GGCGGCGGCG
        V  S  S   G  G  G   G  S  G  G   G  G  T   G  G  G

401   GATCTAGTAT TGTGATGACC CAGACTCCCA CATTCCTGCT TGTTTCAGCA
      G  S  S  I   V  M  T   Q  T  P   T  F  L  L   V  S  A

451   GGAGACAGGG TTACCATAAC CTGCAAGGCC AGTCAGAGTG TGAGTAATGA
        G  D  R   V  T  I  T   C  K  A   S  Q  S   V  S  N  D

501   TGTAGDTTGG TACCAACAGA AGCCAGGGCA GTCTCCTACA CTGCTCATAT
        V  A  W   Y  Q  Q   K  P  G  Q   S  P  T   L  L  I

551   CCTATACATC CAGTCGCTAC GCTGGAGTCC CTGATCGCTT CATTGGCAGT
      S  Y  T  S   S  R  Y   A  G  V   P  D  R  F   I  G  S

601   GGATATGGGA CGGATTTCAC TTTCACCATC AGCACTTTGC AGGCTGAAGA
        G  Y  G   T  D  F  T   F  T  I   S  T  L   Q  A  E  D

651   CCTGGCAGTT TATTTCTGTC AGCAAGATTA TAATTCTCCT CCGACGTTCG
        L  A  V   Y  F  C   Q  Q  D  Y   N  S  P   P  T  F

701   GTGGAGGCAC CAAGCTGGAA ATCAAACGG
      G  G  G  T   K  L  E   I  K  R
```

Figure 1B SEQ ID No 2.

1 AAGCTTCCAC CATGGGATGG AGCTGTATCA TCCTCTTCTT GGTAGCAACA
A S T M G W S C I I L F L V A T

51 GCTACAGGTG TCCACTCCGA GGTCCAGCTT CAGCAGTCTG GACCTGACCT
A T G V H S E V Q L Q Q S G P D L

101 GGTGAAGCCT GGGGCTTCAG TGAAGATATC CTGCAAGGCT TCTGGTTACT
V K P G A S V K I S C K A S G Y

151 CATTCACTGG CTACTACATG CACTGGGTGA AGCAGAGCCA TGGAAAGAGC
S F T G Y Y M H W V K Q S H G K S

201 CTTGAGTGGA TTGGACGTAT TAATCCTAAC AATGGTGTTA CTCTCTACAA
L E W I G R I N P N N G V T L Y N

251 CCAGAAATTC AAGGACAAGG CCATATTAAC TGTAGACAAG TCATCCACCA
Q K F K D K A I L T V D K S S T

301 CAGCCTACAT GGAGCTCCGC AGCCTGACAT CTGAGGACTC TGCGGTCTAT
T A Y M E L R S L T S E D S A V Y

351 TACTGTGCAA GATCTACTAT GATTACGAAC TATGTTATGG ACTACTGGGG
Y C A R S T M I T N Y V M D Y W G

401 TCAAGTAACC TCAGTCACCG TCTCCTCAGG TGGTGGTGGG AGCGGTGGTG
Q V T S V T V S S G G G G S G G

451 GCGGCACTGG CGGCGGCGGA TCTAGTATTG TGATGACCCA GACTCCCACA
G G T G G G G S S I V M T Q T P T

501 TTCCTGCTTG TTTCAGCAGG AGACAGGGTT ACCATAACCT GCAAGGCCAG
F L L V S A G D R V T I T C K A S

551 TCAGAGTGTG AGTAATGATG TAGCTTGGTA CCAACAGAAG CCAGGGCAGT
Q S V S N D V A W Y Q Q K P G Q

601 CTCCTACACT GCTCATATCC TATACATCCA GTCGCTACGC TGGAGTCCCT
S P T L L I S Y T S S R Y A G V P

651 GATCGCTTCA TTGGCAGTGG ATATGGGACG GATTTCACTT TCACCATCAG
D R F I G S G Y G T D F T F T I S

701 CACTTTGCAG GCTGAAGACC TGGCAGTTTA TTTCTGTCAG CAAGATTATA
T L Q A E D L A V Y F C Q Q D Y

Figure 1C SEQ ID NO: 2 Continued

```
751  ATTCTCCTCC GACGTTCGGT GGAGGCACCA AGCTGGAAAT CAAACGGGCC
      N  S  P  P  T  F  G  G  G  T  K  L  E  I  K  R  A

801  TCCACCAAGG GCCCATCGGT CTTCCCCCTG GCACCCTCCT CCAAGAGCAC
      S  T  K  G  P  S  V  F  P  L  A  P  S  S  K  S  T

851  CTCTGGGGGC ACAGCGGCCC TGGGCTGCCT GGTCAAGGAC TACTTCCCCG
      S  G  G  T  A  A  L  G  C  L  V  K  D  Y  F  P

901  AACCGGTGAC GGTGTCGTGG AACTCAGGCG CCCTGACCAG CGGCGTGCAC
     E  P  V  T  V  S  W  N  S  G  A  L  T  S  G  V  H

951  ACCTTCCCGG CTGTCCTACA GTCCTCAGGA CTCTACTCCC TCAGCAGCGT
      T  F  P  A  V  L  Q  S  S  G  L  Y  S  L  S  S  V

1001 GGTGACCGTG CCCTCCAGCA GCTTGGGCAC CCAGACCTAC ATCTGCAACG
      V  T  V  P  S  S  S  L  G  T  Q  T  Y  I  C  N

1051 TGAATCACAA GCCCAGCAAC ACCAAGGTGG ACAAGAAAGT TGAGCCCAAA
     V  N  H  K  P  S  N  T  K  V  D  K  K  V  E  P  K

1101 TCTTGTGACA AAACTCACAC ATGCCCACCG TGCCCAGCAC CTGAACTCCT
      S  C  D  K  T  H  T  C  P  P  C  P  A  P  E  L  L

1151 GGGGGGACCG TCAGTCTTCC TCTTCCCCCC AAAACCCAAG GACACCCTCA
      G  G  P  S  V  F  L  F  P  P  K  P  K  D  T  L

1201 TGATCTCCCG GACCCCTGAG GTCACATGCG TGGTGGTGGA CGTGAGCCAC
     M  I  S  R  T  P  E  V  T  C  V  V  V  D  V  S  H

1251 GAAGACCCTG AGGTCAAGTT CAACTGGTAC GTGGACGGCG TGGAGGTGCA
      E  D  P  E  V  K  F  N  W  Y  V  D  G  V  E  V  H

1301 TAATGCCAAG ACAAAGCCGC GGGAGGAGCA GTACAACAGC ACGTACCGTG
      N  A  K  T  K  P  R  E  E  Q  Y  N  S  T  Y  R

1351 TGGTCAGCGT CCTCACCGTC CTGCACCAGG ACTGGCTGAA TGGCAAGGAG
     V  V  S  V  L  T  V  L  H  Q  D  W  L  N  G  K  E

1401 TACAAGTGCA AGGTCTCCAA CAAAGCCCTC CCAGCCCCCA TCGAGAAAAC
      Y  K  C  K  V  S  N  K  A  L  P  A  P  I  E  K  T

1451 CATCTCCAAA GCCAAAGGGC AGCCCCGAGA ACCACAGGTG TACACCCTGC
      I  S  K  A  K  G  Q  P  R  E  P  Q  V  Y  T  L

1501 CCCCATCCCG GGATGAGCTG ACCAAGAACC AGGTCAGCCT GACCTGCCTG
      P  P  S  R  D  E  L  T  K  N  Q  V  S  L  T  C  L
```

Figure 1D SEQ ID NO: 2 Continued

```
1551 GTCAAAGGCT TCTATCCCAG CGACATCGCC GTGGAGTGGG AGAGCAATGG
      V  K  G   F  Y  P  S   D  I  A   V  E  W   E  S  N  G

1601 GCAGCCGGAG AACAACTACA AGACCACGCC TCCCGTGCTG GACTCCGACG
       Q  P  E   N  N  Y   K  T  T  P   P  V  L   D  S  D

1651 GCTCCTTCTT CCTCTACAGC AAGCTCACCG TGGACAAGAG CAGGTGGCAG
     G  S  F  F   L  Y  S  K  L  T  V   D  K  S   R  W  Q

1701 CAGGGGAACG TCTTCTCATG CTCCGTGATG CATGAGGCTC TGCACAACCA
      Q  G  N   V  F  S  C   S  V  M   H  E  A   L  H  N  H

1751 CTACACGCAG AAGAGCCTCT CCCTGTCTCC GGGTAAATGA GTGCGACGGC
       Y  T  Q   K  S  L   S  L  S  P   G  K  -   V  R  R

1801 CAAGCTT
     P  S
```

Figure 2A SEQ ID NO: 3

```
ATGGGCCACA CACGGAGGCA GGGAACATCA CCATCCAAGT GTCCATACCT    50
 M  G  H   T  R  R  Q   G  T  S   P  S  K   C  P  Y  L
CAATTTCTTT CAGCTCTTGG TGCTGGCTGG TCTTTCTCAC TTCTGTTCAG    100
 N  F  F   Q  L  L   V  L  A  G   L  S  H   F  C  S
GTGTTATCCA CGTGACCAAG GAAGTGAAAG AAGTGGCAAC GCTGTCCTGT    150
G  V  I  H   V  T  K   E  V  K   E  V  A  T   L  S  C
GGTCACAATG TTTCTGTTGA AGAGCTGGCA CAAACTCGCA TCTACTGGCA    200
 G  H  N   V  S  V  E   E  L  A   Q  T  R   I  Y  W  Q
AAAGGAGAAG AAAATGGTGC TGACTATGAT GTCTGGGGAC ATGAATATAT    250
 K  E  K   K  M  V   L  T  M  M   S  G  D   M  N  I
GGCCCGAGTA CAAGAACCGG ACCATCTTTG ATATCACTAA TAACCTCTCC    300
W  P  E  Y   K  N  R   T  I  F   D  I  T  N   N  L  S
ATTGTGATCC TGGCTCTGCG CCCATCTGAC GAGGGCACAT ACGAGTGTGT    350
 I  V  I   L  A  L  R   P  S  D   E  G  T   Y  E  C  V
TGTTCTGAAG TATGAAAAAG ACGCTTTCAA GCGGGAACAC CTGGCTGAAG    400
 V  L  K   Y  E  K   D  A  F  K   R  E  H   L  A  E
TGACGTTATC AGTCAAAGCT GACTTCCCTA CACCTAGTAT ATCTGACTTT    450
V  T  L  S   V  K  A   D  F  P   T  P  S  I   S  D  F
GAAATTCCAA CTTCTAATAT TAGAAGGATA ATTTGCTCAA CCTCTGGAGG    500
 E  I  P   T  S  N  I   R  R  I   I  C  S   T  S  G  G
TTTTCCAGAG CCTCACCTCT CCTGGTTGGA AAATGGAGAA GAATTAAATG    550
 F  P  E   P  H  L   S  W  L  E   N  G  E   E  L  N
CCATCAACAC AACAGTTTCC CAAGATCCTG AAACTGAGCT CTATGCTGTT    600
A  I  N  T   T  V  S   Q  D  P   E  T  E  L   Y  A  V
AGCAGCAAAC TGGATTTCAA TATGACAACC AACCACAGCT TCATGTGTCT    650
 S  S  K   L  D  F  N   M  T  T   N  H  S   F  M  C  L
CATCAAGTAT GGACATTTAA GAGTGAATCA GACCTTCAAC TGGAATACAA    700
  I  K  Y   G  H  L   R  V  N  Q   T  F  N   W  N  T
```

Figure 2B SEQ ID NO: 3 Continued

```
CCAAGCAAGA GCATTTTCCT GATGGAGGCG GGGGATCCGA GGTCCAGCTT      750
T  K  Q  E   H  F  P   D  G  G   G  G  S  E   V  Q  L

CAGCAGTCTG GACCTGACCT GGTGAAGCCT GGGGCTTCAG TGAAGATATC      800
 Q  Q  S   G  P  D  L   V  K  P   G  A  S   V  K  I  S

CTGCAAGGCT TCTGGTTACT CATTCACTGG CTACTACATG CACTGGGTGA      850
  C  K  A   S  G  Y   S  F  T  G   Y  Y  M   H  W  V

AGCAGAGCCA TGGAAAGAGC CTTGAGTGGA TTGGACGTAT TAATCCTAAC      900
K  Q  S  H   G  K  S   L  E  W   I  G  R  I   N  P  N

AATGGTGTTA CTCTCTACAA CCAGAAATTC AAGGACAAGG CCATATTAAC      950
 N  G  V   T  L  Y  N   Q  K  F   K  D  K   A  I  L  T

TGTAGACAAG TCATCCACCA CAGCCTACAT GGAGCTCCGC AGCCTGACAT      1000
  V  D  K   S  S  T   T  A  Y  M   E  L  R   S  L  T

CTGAGGACTC TGCGGTCTAT TACTGTGCAA GATCTACTAT GATTACGAAC      1050
S  E  D  S   A  V  Y   Y  C  A   R  S  T  M   I  T  N

TATGTTATGG ACTACTGGGG TCAAGTAACC TCAGTCACCG TCTCCTCAGG      1100
 Y  V  M   D  Y  W  G   Q  V  T   S  V  T   V  S  S  G

TGGTGGTGGG AGCGGTGGTG GCGGCACTGG CGGCGGCGGA TCTAGTATTG      1150
  G  G  G   S  G  G   G  G  T  G   G  G  G   S  S  I

TGATGACCCA GACTCCCACA TTCCTGCTTG TTTCAGCAGG AGACAGGGTT      1200
V  M  T  Q   T  P  T   F  L  L   V  S  A  G   D  R  V

ACCATAACCT GCAAGGCCAG TCAGAGTGTG AGTAATGATG TAGCTTGGTA      1250
 T  I  T   C  K  A  S   Q  S  V   S  N  D   V  A  W  Y

CCAACAGAAG CCAGGGCAGT CTCCTACACT GCTCATATCC TATACATCCA      1300
  Q  Q  K   P  G  Q   S  P  T  L   L  I  S   Y  T  S

GTCGCTACGC TGGAGTCCCT GATCGCTTCA TTGGCAGTGG ATATGGGACG      1350
S  R  Y  A   G  V  P   D  R  F   I  G  S  G   Y  G  T

GATTTCACTT TCACCATCAG CACTTTGCAG GCTGAAGACC TGGCAGTTTA      1400
 D  F  T   F  T  I  S   T  L  Q   A  E  D   L  A  V  Y

TTTCTGTCAG CAAGATTATA ATTCTCCTCC GACGTTCGGT GGAGGCACCA      1450
  F  C  Q   Q  D  Y   N  S  P  P   T  F  G   G  G  T
```

Figure 2C SEQ ID NO: 3 Continued

```
AGCTGGAAAT CAAATAA
K  L  E  I   K
```

B7-1.5T4.1

B7-1.5T4.2

Figure 4A seq id No. 4.

Molecule Name-: B7-2(1-241) 738 bps DNA Linear
Sequence Printed: 1-738 (Full) Date Printed 02 Jun 1997
Description:

```
1     ATGGGACTGA GTAACATTCT CTTTGTGATG GCCTTCCTGC TCTCTGGTGC
       M  G  L   S  N  I  L   F  V  M   A  F  L   L  S  G  A

51    TGCTCCTCTG AAGATTCAAG CTTATTTCAA TGAGACTGCA GACCTGCCAT
        A  P  L   K  I  Q   A  Y  F  N   E  T  A   D  L  P

101   GCCAATTTGC AAACTCTCAA AACCAAAGCC TGAGTGAGCT AGTAGTATTT
       C  Q  F   A  N  S  Q   N  Q  S  L  S  E  L   V  V  F

151   TGGCAGGACC AGGAAAACTT GGTTCTGAAT GAGGTATACT TAGGCAAAGA
       W  Q  D   Q  E  N  L   V  L  N   E  V  Y   L  G  K  E

201   GAAATTTGAC AGTGTTCATT CCAAGTATAT GGGCCGCACA AGTTTTGATT
        K  F  D   S  V  H   S  K  Y  M   G  R  T   S  F  D

251   CGGACAGTTG GACCCTGAGA CTTCACAATC TTCAGATCAA GGACAAGGGC
      S  D  S  W   T  L  R   L  H  N   L  Q  I  K   D  K  G

301   TTGTATCAAT GTATCATCCA TCACAAAAAG CCCACAGGAA TGATTCGCAT
       L  Y  Q   C  I  I  H   H  K  K   P  T  G   M  I  R  I

351   CCACCAGATG AATTCTGAAC TGTCAGTGCT TGCTAACTTC AGTCAACCTG
        H  Q  M   N  S  E   L  S  V  L   A  N  F   S  Q  P

401   AAATAGTACC AATTTCTAAT ATAACAGAAA ATGTGTACAT AAATTTGACC
      E  I  V  P   I  S  N   I  T  E   N  V  Y  I   N  L  T

451   TGCTCATCTA TACACGGTTA CCCAGAACCT AAGAAGATGA GTGTTTTGCT
       C  S  S   I  H  G  Y   P  E  P   K  K  M   S  V  L  L

501   AAGAACCAAG AATTCAACTA TCGAGTATGA TGGTATTATG CAGAAATCTC
        R  T  K   N  S  T   I  E  Y  D   G  I  M   Q  K  S

551   AAGATAATGT CACAGAACTG TACGACGTTT CCATCAGCTT GTCTGTTTCA
      Q  D  N  V   T  E  L   Y  D  V   S  I  S  L   S  V  S

601   TTCCCTGATG TTACGAGCAA TATGACCATC TTCTGTATTC TGGAAACTGA
       F  P  D   V  T  S  N   M  T  I   F  C  I   L  E  T  D

651   CAAGACGCGG CTTTTATCTT CACCTTTCTC TATAGAGCTT GAGGACCCTC
        K  T  R   L  L  S   S  P  F  S   I  E  L   E  D  P
```

Figure 4B SEQ ID NO: 4 Continued

```
701  AGCCTCCCCC AGACCACATT CCTGGAGGCG GGGGATCC
      Q  P  P  P   D  H  I   P  G  G   G  G  S
```

VECTOR

This application is a continuation of U.S. patent application Ser. No. 11/380,188, filed Apr. 25, 2006, which is a continuation of U.S. patent application Ser. No. 10/104,522, filed Mar. 22, 2002, which is a divisional of U.S. patent application Ser. No. 09/445,375, filed Mar. 21, 2000, which is the U.S. national phase of International Application No. PCT/GB98/01627, which claims the benefit of priority of United Kingdom Patent Applications Nos. 9711579.4, 9713150.2 and 9714230.1, filed on Jun. 4, 1997, Jun. 20, 1997 and Jul. 4, 1997, respectively.

The present invention relates to a vector, preferably for use in medicine.

As it is well known in the art, a vector is a tool that allows or faciliates the transfer of an entity from one environment to another. By way of example, some vectors used in recombinant DNA techniques allow entities—such as a segment of DNA (such as a heterologous DNA segment, such as a heterologous cDNA segment)—to be transferred into a target cell. Optionally, once within the target cell, the vector may then serve to maintain the heterologous DNA within the cell or may act as a unit of DNA replication. Examples of vectors used in recombinant DNA techniques include plasmids, chromosomes, artificial chromosomes or viruses.

Thus, vectors can be used to deliver proteins and/or nucleotide sequences to targeted cells, such as tumour cells.

However, as it is well known, nucleotide sequences and proteins are complex molecules which may be produced from biological sources, most usually from genetically engineered organisms or cell cultures. Furthermore, the procedures for the production of nucleotide sequences and proteins can be complicated, labour intensive and costly. Furthermore, pharmacological properties and other aspects of the function of some proteins—such as immunoglobulins derived from non-human biological sources—and nucleotide sequences may frequently differ in important ways from the activity of the corresponding natural human immunoglobulins produced in human cells. By way of background information, an immunoglobulin is a member of a family of related multimeric proteins which are normally secreted from cells of the B-lymphocyte lineage of a vertebrate, whose typical function is to bind specifically with a region of a macromolecule identified as non-self. Immunoglobulins represent a major component of the immune response repertoire of the organism and are synonymous with"antibodies". One major cause of such differences in activity may be due to variations in the pattern of glycosylation of proteins derived from different species (reviewed in Bebbington 1995; In Monoclonal Antibodies: the second generation ed. H. Zola pg 165-181). Furthermore, systemic administration of proteins (especially those containing toxin domains) and nucleotide sequences can induce additional pharmacokinetic and toxicological problems (reviewed in Scheinberg and Chapman 1995. In Monoclonal antibodies (ed. Birch and Lennox) Chapter 2.1).

Thus, the present invention seeks to provide an improved vector system for delivering a nucleotide sequence of interest and/or a product expressed by the same.

According to a first aspect of the present invention there is provided a vector comprising a nucleotide sequence ("NS") coding for a tumour interacting protein ("TIP") and optionally comprising a nucleotide sequence of interest ("NOI") which NOI encodes a product of interest ("POI"); wherein the TIP is capable of recognising a tumour, such that in use the vector is capable of delivering the NOI and/or the POI to the tumour.

According to a second aspect of the present invention there is provided a method of delivering a nucleotide sequence of interest ("NOI") and/or a product of interest ("POI") encoded by same to a tumour, wherein the NOI and/or POI are delivered to the tumour by use of a vector comprising the NOI and/or expressing the POI; wherein the NOI and/or the POI is capable of recognising a tumour; wherein the NOI and/or the POI is delivered to the tumour; and wherein the vector is a vector according to the present invention.

According to a third aspect of the present invention there is provided the use of a vector to deliver a nucleotide sequence of interest ("NOI") and/or a product of interest ("POI") encoded by same to a tumour, wherein the NOI and/or POI are delivered to the tumour by use of the vector which comprises the NOI and/or expresses the POI; wherein the NOI and/or the POI is capable of recognising a tumour when the NOI and/or the POI is delivered to the tumour; and wherein the vector is a vector according to the present invention.

According to a fourth aspect of the present invention there is provided a method of treating a subject in need of same, the method comprising delivering a nucleotide sequence of interest ("NOI") and/or a product of interest ("POI") encoded by same to a tumour, wherein the NOI and/or POI are delivered to the tumour by use of a vector comprising the NOI and/or expressing the POI; wherein the NOI and/or the POI is capable of recognising a tumour; wherein the NOI and/or the POI is delivered to the tumour; and wherein the vector is a vector according to the present invention.

According to a fifth aspect of the present invention there is provided the use of a genetic vectors to deliver a therapeutic gene encoding a TIP—preferably a tumour binding protein ("TBP")—more preferably a secretable TIP (preferably a secretable TBP)—to the interior of a tumour mass.

According to a sixth aspect of the present invention there is provided a gene delivery system for targeting one or more genes encoding a TIP (preferably a TBP) to a tumour, comprising a genetic vector encoding a TIP (preferably a TBP) and an in vivo gene-delivery system.

According to a seventh aspect of the present invention there is provided a method of treating cancer comprising administering a TIP (preferably a TBP) gene or genes in a gene delivery system according to the present invention either systemically or directly to the site of a tumour.

According to an eighth aspect of the present invention there is provided a gene delivery system for introducing one or more genes encoding a TIP (preferably a TBP) into cells of the haematopoietic (preferably myeloid haematopoietic) cell lineage either in vivo or ex vivo.

According to a ninth aspect of the present invention there is provided a method for treating cancer in a mammal, comprising administering to an individual a gene delivery system according to the present invention that is capable of expressing a TBP in cells derived from a haematopoietic (preferably myeloid haematopoietic) origin.

According to a tenth aspect of the present invention there is provided a genetic vector comprising a therapeutic gene or genes encoding a TIP (preferably a TBP), operably linked to an expression regulatory element selectively functional in a cell type present within a tumour mass.

According to an eleventh aspect of the present invention there is provided a genetic vector comprising a therapeutic gene or genes is delivered to the interior of the tumour wherein the therapeutic gene encodes a TIP (preferably a TBP), which additionally contains one or more effector domains.

According to a twelfth aspect of the present invention there is provided a method of treating cancer in a mammal which comprises administering to an individual a combination of a cytokine or a cytokine-encoding gene and one or more TIP (preferably a TBP) genes according to any of the previous aspects of the invention.

According to a thirteenth aspect of the present invention there is provided the delivery of TIP—(preferably a TBP-) encoding genes to the site of a tumour.

Preferably the vector comprises the NOI.

In one preferred aspect, the vector is expressing the POI.

The vector of the present invention may be useful for inter alia medical applications—such as diagnostic or therapeutic applications.

Preferably the NOI is a therapeutic NOI and/or the POI is a therapeutic POI.

On occasions in the following text, the NS and NOI may be individually or collectively referred to as being a gene.

The NS and NOI can be any suitable nucleotide sequence. For example, independently they can be DNA or RNA—which may synthetically prepared or may be prepared by use of recombinant DNA techniques or may be isolated from natural sources or may be combinations thereof. The NOI may be a sense sequence or an antisense sequence.

There may be a plurality of NSs or NOIs, which may be directly or indirectly joined to each other, or combinations thereof. Thus, the expressed product may have two or more effector domains (which may be the same or different) and/or two or more TIP domains (which may be the same or different).

Preferably in use the vector is capable of delivering the NOI and/or the POI to the interior of a tumour mass.

In addition to cancerous cell, the cell types present within a tumour mass include but are not limited to macrophages, lymphocytes, tumour infiltrating lymphocyes, endothelial cells etc.

Preferably the NS and/or the TIP comprises at least one tumour binding domain capable of interacting with at least one tumour associated cell surface molecule (“TACSM”).

In accordance with the present invention the TACSM can include but is not limited to a cell surface molecule which plays a role in tumour cell growth, migration or metastasis, a receptor for adhesive proteins such as the integrin vitronectin receptor, a growth factor receptor (such as epidermal growth factor (EGF) receptor, platelet-derived growth factor (PDGF) receptor, fibroblast-derived growth factor (FDGF) receptor, nerve growth factor receptor, insulin-like growth factor (IGF-1) receptor; a plasminogen activator; a metalloproteinase (such as colllagenase) 5T4 antigen; a tumour specific carbohydrate moiety; an oncofetal antigen; a mucin; a growth factor receptor; a glycoprotein; and an antigen restricted in its tissue distribution.

Preferably the TACSM is selectively expressed on one cell type or on a restrictive number of cell types.

Preferably in use the vector is capable of delivering the NOI and/or the POI to a selective tumour site.

Preferably the TIP is or comprises a tomour binding protein (“TBP”).

Preferably the TIP is a TBP.

Examples of a TBP include: an adhesion molecule such as Intercellular adhesion molecule, ICAM-1, ICAM-2, LFA-1, LFA-2, LFA-3, LECAM-1, VLA-4, ELAM, N-CAM, N-cadherin, P-Selectin, CD44 and its variant isoforms (in particular CD44v6, CD44v7-8), CD56; a growth factor receptor ligand such epidermal growth factor (EGF), Platelet-derived growth factor (PDGF), Fibroblast-derived growth factor (FDGF), Nerve growth factor, vasopressin, insulin, insulin-like growth factor (IGF-1), hepatocyte growth factor, nerve growth factor, human growth factor, brain derived growth factor, ciliary neutrophic factor, glial cell line-derived growth factor; heavy and light chain sequences from an immunoglobulin (Ig) variable region (from human and animal sources), engineered antibody or one from a phage display library. A phage display library is a technique of expressing immunoglobulin genes in bacteriophage has been developed as a means for obtaining antibodies with the desired binding specificities. Expression systems, based on bacteriophage lambda, and more recently filamentous phage have been developed. The bacteriophage expression systems can be designed to allow heavy and light chains to form random combinations which are tested for their ability to bind the desired antigen.

The TBP may contain an effector domain which is activated on binding of the TPB to the TASCM. The effector domain or momains may be activated on binding of the TBP to a TASCM leading to inhibition of tumour cell proliferation, survival or dissemination. The effector domain may possess enzymatic activity (such as a pro-drug activating enzyme) or the effector domain may include a toxin, or an immune enhancer, such as a cytokine/lymphokine such as those listed above.

Preferably the TBP comprises one or more binding domains capable of interacting with one or more TACSMs which are present on the cancerous cells—which TACSMs may be the same or different.

The term “interacting” includes direct binding, leading to a biological effect as a result of such binding.

Preferably the TIP is or comprises at least part of an antibody.

As is well known, antibodies play a key role in the immune system. In brief, the immune system works in three fundamentally different ways: by humoral immunity, by cellular immunity and by secretion of stimulatory proteins, called lymphokines Humoral immunity relies on proteins collectively called immunoglobulin which constitute about 20% of the proteins in the blood. A singly immunoglobulin molecule is called an antibody but “antibody” is also used to mean many different molecules all directed against the same target molecule. Humoral immunity also involves complement, a set of proteins that are activated to kill bacteria both nonspecifically and in conjunction with antibody.

In cellular immunity, intact cells are responsible for recognition and elimination reactions. The body’s first line of defense is the recognition and killing of microorganisms by phagocytes, cells specialised for the ingestion and digestion of unwanted material. These cells include neutrophils and macrophages. A key role of antibodies is to help phagocytes recognise and destroy foreign materials.

In order to perform these functions, the antibody is divided into two regions: binding (Fab) domains that interact with the antigen and effector (Fc) domains that signal the initiation of processes such as phagocytosis. Each antibody molecule consists of two classes of polypeptide chains, light (L) chains and heavy (H) chains. A single antibody has two identical copies of the L chain and two of the H chain. The N-terminal domain from each chain forms the variable regions, which constitute the antigen-binding sites. The C-terminal domain is called the constant region. The variable domains of the H ($V_H$) and L ($V_L$) chains constitute an Fv unit and can interact closely to form a single chain Fv (ScFv) unit. In most H chains, a hinge region is found. This hinge region is flexible and allows the Fab binding regions to move freely relative to the rest of the molecule. The hinge region is also the place on the molecule most susceptible to the action of protease which can split the antibody into the antigen binding site (Fab) and the effector (Fc) region.

The domain structure of the antibody molecule is favourable to protein engineering, facilitating the exchange between molecules of functional domains carrying antigen-binding activities (Fabs and Fvs) or effector functions (Fc). The structure of the antibody also makes it easy to produce antibodies with an antigen recognition capacity joined to molecules such as toxins, lymphocytes or growth factors.

Monoclonal antibodies are homogenous antibodies of the same antigenic specificity representing the product of a single clone of antibody-producing cells. It was recognised that monoclonal antibodies offered the basis for human therapeutic products. However, although mouse antibodies are similar to human antibodies, they are sufficiently different that they are recognised by the immune system as foreign bodies, thereby giving rise to an immunological response. This human-anti-mouse-antibody (HAMA) response limits the usefulness of mouse antibodies as human therapeutic products.

Chimeric antibody technology involves the transplantation of whole mouse antibody variable domains onto human antibody constant domains. Chimeric antibodies are less immunogenic than mouse antibodies but they retain their antibody specificity and show reduced HAMA responses.

In chimeric antibodies, the variable region remains completely murine. However, the structure of the antibody makes it possible to produce variable regions of comparable specificity which are predominantly human in origin. The antigen-combining site of an antibody is formed from the six complementarity-determining regions (CDRs) of the variable portion of the heavy and light chains. Each antibody domain consists of seven antiparallel β-sheets forming a β-barrel with loops connecting the β-strands. Among the loops are the CDR regions. It is feasible to more the CDRs and their associated specificity from one scaffolding β-barrel to another. This is called CDR-grafting. CDR-grafted antibodies appear in early clinical studies not to be as strongly immunogenic as either mouse or chimeric antibodies. Moreover, mutations may be made outside the CDR in order to increase the binding activity thereof, as in so-called humanised antibodies.

Fab, Fv, and single chain Fv (ScFv) fragments with VH and VL joined by a polypeptide linker exhibit specificities and affinities for antigen similar to the original monoclonal antibodies. The ScFv fusion proteins can be produced with a nonantibody molecule attached to either the amino or carboxy terminus. In these molecules, the Fv can be used for specific targeting of the attached molecule to a cell expressing the appropriate antigen. Bifunctional antibodies can also be created by engineering two different binding specificities into a single antibody chain. Bifunctional Fab, Fv and ScFv antibodies may comprise engineered domains such as CDR grafted or humanised domains.

In virally directed enzyme therapy (VDEPT), a foreign gene is delivered to normal and cancerous cells by a viral vector—such as a retroviral vector. The foreign gene codes for an enzyme that can convert a non-toxic prodrug (e.g. 5-fluorocytosine) to a toxic metabolite (5-fluorouracil) that will kill those cells making it (Sikora et at 1994 Ann New York Acad Sci 71b: 115-124). If the promoter utilised is tumour specific, then the toxic product will only be synthesised in the tumour cells. Studies in animal models have demonstrated that this type of treatment can deliver up to 50-fold more drug than by conventional means (Connors and Knox 1995 1995 Stem Cells 13: 501-511). A variation of this technique uses tumour associated antibodies conjugated to prodrug converting enzymes to provide specific delivery to tumours. This method is referred to as antibody-directed enzyme prodrug therapy (ADEPT) (Maulik S and Patel S D "Molecular Biotechnology" 1997 Wiley-Liss Inc. pp 45).

A large number of monoclonal antibodies and immunoglobulin-like molecules are known which bind specifically to antigens present on the surfaces of particular cell types such as tumour cells. Procedures for identifying, characterising, cloning and engineering these molecules are well established, for example using hybridomas derived from mice or transgenic mice, phage-display libraries or scFv libraries. Genes encoding immunoglobulins or immunoglobulin-like molecules can be expressed in a variety of heterologous expression systems. Large glycosylated proteins including immunoglobulins are efficiently secreted and assembled from eukaryotic cells, particularly mammalian cells. Small, non-glycosylated fragments such as Fab, Fv, or scFv fragments can be produced in functional form in mammalian cells or bacterial cells.

The immunoglobulin or immunoglobulin-like molecule may be derived from a human antibody or an engineered, humanised rodent antibody such as a CDR-grafted antibody or may be derived from a phage-display library or may be a synthetic immunoglobulin-like molecule.

The antigen-binding domain may be comprised of the heavy and light chains of an immunoglobulin, expressed from separate genes, or may use the light chain of an immunoglobulin and a truncated heavy chain to form a Fab or a $F(ab)_2$ fragment. Alternatively, truncated forms of both heavy and light chains may be used which assemble to form a Fv fragment. An engineered scFv fragment may also be used, in which case, only a single gene is required to encode the antigen-binding domain. In one preferred aspect, the antigen-binding domain is formed from a Fv or a scFv.

When a pathogen invades the body, lymphocytes respond with three types of reaction. The lymphocytes of the humoral system (B cells) secrete antibodies that can bind to the pathogen, signalling its degradation by macrophages and other cells. The lymphocytes of the cellular system (T cells) carry out two major types of functions. Cytotoxic T lymphocytes (CTLs) develop the ability to directly recognise and kill the cells infected by the pathogen. Helper T cells (TH cells) independently recognise the pathogen and secrete protein factors (lymphokines) that stimulate growth and responsiveness of B cells, T cells, and macrophages, thus greatly strengthening the power of the immune response.

Thus, in one preferred aspect, the TIP comprises an immunoglobulin, or a part thereof, or a bioisostere thereof.

In a preferred embodiment, the TIP comprises IgG and/or IgE, or a part thereof, or a bioisostere thereof.

In a more preferred embodiment, the TIP comprises IgE, or a part thereof, or a bioisostere thereof.

Preferably the TIP recognises a trophoblast cell surface antigen.

Preferably the TIP recognises the 5T4 antigen.

The trophoblast cell surface antigen, originally defined by monoclonal antibody 5T4 (Hole and Stern 1988 Br. J. Cancer 57; 239-246), is expressed at high levels on the cells of a wide variety of human carcinomas (Myers et al. 1994 J. Biol. Chem. 269; 9319-9324) but, in normal tissues of non-pregnant individuals, is essentially restricted to low level expression on a few specialised epithelia (Myers et al. ibid. and references therein). The 5T4 antigen has been implicated in contributing to the development of metastatic potential and therefore antibodies specifically recognising this molecule may have clinical relevance in the treatment of tumours expressing the antigen.

The variable region of the 5T4 monoclonal antibody can also be humanised by a number of techniques, which are known in the art, including grafting of the CDR region sequences on to a human backbone. These can then be used to construct an intact humanised antibody or a humanised single chain antibody (Sab), such as an ScFv coupled to an Fc region (see Antibody Engineering: a practical approach, ed McCafferty et al. 1996 OUP).

Here the term Sab is not limited to just a human or a humanised single chain antibody. Preferably, however the Sab is a human single chain antibody or a humanised single chain antibody, or part thereof—such as ScFv coupled to an Fc region.

Preferably the NS and NOI and/or the TIP and POI are linked together.

Preferably the TIP and POI are directly linked together.

Preferably any one or more of the NS, NOI, TIP, and POI further comprise at least one additional functional component.

Preferably, at least the TIP and/or POI further comprise at least one additional functional component.

Preferably the additional functional component is selected from any one or more of a signalling entity (such as a signal peptide), an immune enhancer, a toxin, or a biologically active enzyme.

In a preferred aspect the POI is a secretable POI. Thus, in this aspect of the present invention, preferably, the additional functional component is at least an entity capable of causing the POI to be secreted—such as a signalling entity.

Another preferred additional component is a promoter.

The term "promoter" is used in the normal sense of the art, e.g. an RNA polymerase binding site in the Jacob-Monod theory of gene expression.

Preferably the vector comprises a tumour specific promoter enhancer.

Other preferred additional components include entities enabling efficient expression of the POI. For example, the additional component may be an enhancer. Here, the term enhancer includes a DNA sequence which binds to other protein components of the transcription initiation complex and thus facilitates the initiation of transcription directed by its associated promoter.

Preferably the vector is used to deliver the NOI and/or POI ex vivo and/or in vivo to the tumour.

The vector of the present invention is useful in gene therapy for delivering the NOI and/or the POI to a selective site.

Gene therapy includes any one or more of: the addition, the replacement, the deletion, the supplementation, the manipulation etc. of one or more nucleotide sequences in, for example, one or more targeted sites—such as targeted cells. If the targeted sites are targeted cells, then the cells may be part of a tissue or an organ. General teachings on gene therapy may be found in Molecular Biology (Ed Robert Meyers, Pub VCH, such as pages 556-558).

By way of further example, gene therapy also provides a means by which any one or more of: a nucleotide sequence, such as a gene, can be applied to replace or supplement a defective gene; a pathogenic gene or gene product can be eliminated; a new gene can be added in order, for example, to create a more favourable phenotype; cells can be manipulated at the molecular level to treat cancer (Schmidt-Wolf and Schmidt-Wolf, 1994, Annals of Hematology 69; 273-279) or other conditions—such as immune, cardiovascular, neurological, inflammatory or infectious disorders; antigens can be manipulated and/or introduced to elicit an immune response—such as genetic vaccination.

The vector of the present invention may be a viral vector or a non-viral vector. Non-viral delivery systems include but are not limited to DNA transfection methods. Here transfection includes a process using a non-viral vector to deliver a gene to a target mammalian cell. Typical transfection methods include electroporation, DNA biolistics, lipid-mediated transfection, compacted DNA-mediated transfection, liposomes, immunoliposomes, lipofectin, cationic agent-mediated, cationic facial amphiphiles (CFAs) (Nature Biotechnology 1996 14; 556), and combinations thereof. Viral delivery systems include but are not limited to adenovirus vector, an adeno-associated viral (AAV) vector, a herpes viral vector, retroviral vector, lentiviral vector, baculoviral vector. Other examples of vectors include ex vivo delivery systems—which include but are not limited to DNA transfection methods such as electroporation, DNA biolistics, lipid-mediated transfection, compacted DNA-mediated transfection).

Preferably the vector is a viral vector.

Preferably the vector is a retroviral vector.

In recent years, retroviruses have been proposed for use in gene therapy. Essentially, retroviruses are RNA viruses with a life cycle different to that of lytic viruses. In this regard, when a retrovirus infects a cell, its genome is converted to a DNA form. In slightly more detail, a retrovirus is a virus which contains genomic RNA which on entry into a host cell is converted to a DNA molecule by a reverse transcriptase enzyme. The DNA copy serves as a template for the production of new RNA genomes and virally encoded proteins necessary for the assembly of infectious viral particles. Thus, a retrovirus is an infectious entity that replicates through a DNA intermediate.

There are many retroviruses and examples include: murine leukemia virus (MLV), human immunodeficiency virus (HIV), equine infectious anaemia virus (EIAV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV).

A detailed list of retroviruses may be found in Coffin et at ("Retroviruses"1997 Cold Spring Harbour Laboratory Press Eds: J M Coffin, S M Hughes, H E Varmus pp 758-763).

Details on the genomic structure of some retroviruses may be found in the art. By way of example, details on HIV may be found from the NCBI Genbank (i.e. Genome Accession No. AF033819).

All retroviruses contain three major coding domains, gag, pol, env, which code for essential virion proteins. Nevertheless, retroviruses may be broadly divided into two categories: namely, "simple" and "complex". These categories are distinguishable by the organisation of their genomes. Simple retroviruses usually carry only this elementary information. In contrast, complex retroviruses also code for additional regulatory proteins derived from multiple spliced messages.

Retroviruses may even be further divided into seven groups. Five of these groups represent retroviruses with oncogenic potential. The remaining two groups are the lentiviruses and the spumaviruses. A review of these retroviruses is presented in "Retroviruses" (1997 Cold Spring Harbour Laboratory Press Eds: J M Coffin, S M Hughes, H E Varmus pp 1-25).

All oncogenic members except the human T-cell leukemia virus-bovine leukemia virus group (HTLV-BLV) are simple retroviruses. HTLV, BLV and the lentiviruses and spumaviruses are complex. Some of the best studied oncogenic retroviruses are Rous sarcoma virus (RSV), mouse mammary tumour virus (MMTV) and murine leukemia virus (MLV) and the human T-cell leukemia virus (HTLV).

The lentivirus group can be split even further into "primate" and "non-primate". Examples of primate lentiviruses include the human immunodeficiency virus (HIV), the causative agent of human auto-immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiencey virus (FIV) and bovine immunodeficiencey virus (BIV).

A distinction between the lentivirus family and other types of retroviruses is that lentiviruses have the capability to infect both dividing and non-dividing cells (Lewis et at 1992 EMBO. J 11; 3053-3058, Lewis and Emerman 1994 J. Virol. 68: 510-516). In contrast, other retroviruses—such as MLV—are unable to infect non-dividing cells such as those that make up, for example, muscle, brain, lung and liver tissue.

During the process of infection, a retrovirus initially attaches to a specific cell surface receptor. On entry into the susceptible host cell, the retroviral RNA genome is then copied to DNA by the virally encoded reverse transcriptase which is carried inside the parent virus. This DNA is transported to the host cell nucleus where it subsequently integrates into the host genome. At this stage, it is typically referred to as the provirus. The provirus is stable in the host chromosome during cell division and is transcribed like other cellular proteins. The provirus encodes the proteins and packaging machinery required to make more virus, which can leave the cell by a process sometimes called"budding".

As already indicated, each retroviral genome comprises genes called gag, pol and env which code for virion proteins and enzymes. These genes are flanked at both ends by regions called long terminal repeats (LTRs). The LTRs are responsible for proviral integration, and transcription. They also serve as enhancer-promoter sequences. In other words, the LTRs can control the expression of the viral gene. Encapsidation of the retroviral RNAs occurs by virtue of a psi sequence located at the 5' end of the viral genome.

The LTRs themselves are identical sequences that can be divided into three elements, which are called U3, R and U5. U3 is derived from the sequence unique to the 3' end of the RNA. R is derived from a sequence repeated at both ends of the RNA and U5 is derived from the sequence unique to the 5' end of the RNA. The sizes of the three elements can vary considerably among different retroviruses.

Figure 5:
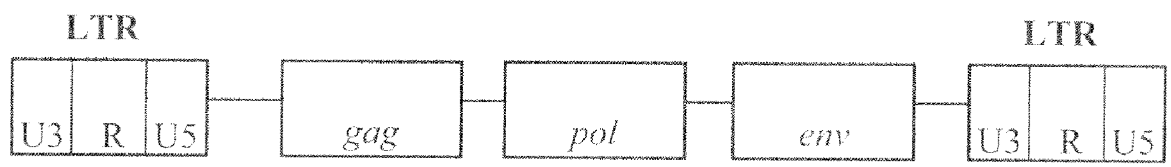

For ease of understanding, a simple, generic diagram (not to scale) of a retroviral genome showing the elementary features of the LTRs, gag, pol and env is presented in FIG. 5.

For the viral genome, the site of transcription initiation is at the boundary between U3 and R in the left hand side LTR (as shown above) and the site of poly (A) addition (termination) is at the boundary between R and U5 in the right hand side LTR (as shown above). U3 contains most of the transcriptional control elements of the provirus, which include the promoter and multiple enhancer sequences responsive to cellular and in some cases, viral transcriptional activator proteins. Some retroviruses have any one or more of the following genes that code for proteins that are involved in the regulation of gene expression: tat, rev, tax and rex.

a p As shown in the diagram above, the basic molecular organisation of a retroviral RNA genome is (5') R-U5-gag, pol, env-U3-R (3'). In a retroviral vector genome gag, pol and env are absent or not functional. The R regions at both ends of the RNA are repeated sequences. U5 and U3 represent sequences unique, respectively, to the 5' and 3' ends of the RNA genome. These three sets of end sequences go to form the long terminal repeats (LTRs) in the proviral DNA, which is the form of the genome which integrates into the genome of the infected cell. The LTRs in a wild type retrovirus consist of (5') U3-R-U5 (3'), and thus U3 and U5 both contain sequences which are important for proviral integration. Other essential sequences required in the genome for proper functioning include a primer binding site for first strand reverse transcription, primer binding site for second strand reverse transcription and a packaging signal.

With regard to the structural genes gag, pol and env themselves and in slightly more detail, gag encodes the internal structural protein of the virus. Gag is proteolytically processed into the mature proteins MA (matrix), CA (capsid), NC (nucleocapsid). The gene pol encodes the reverse transcriptase (RT), which contains both DNA polymerase, and associated RNase H activities and integrase (IN), which mediates replication of the genome. The gene env encodes the surface (SU) glycoprotein and the transmembrane (TM) protein of the virion, which form a complex that interacts specifically with cellular receptor proteins. This interaction leads ultimately to fusion of the viral membrane with the cell membrane.

The envelope protein is a viral protein which coats the viral particle and plays an essential role in permitting viral entry into a target cell. The envelope glycoprotein complex of retroviruses includes two polypeptides: an external, glycosylated hydrophilic polypeptide (SU) and a membrane-spanning protein (TM). Together, these form an oligomeric "knob" or "knobbed spike" on the surface of a virion. Both polypeptides are encoded by the env gene and are synthesised in the form of a polyprotein precursor that is proteolytically cleaved during its transport to the cell surface. Although uncleaved Env proteins are able to bind to the receptor, the cleavage event itself is necessary to activate the fusion potential of the protein, which is necessary for entry of the virus into the host cell. Typically, both SU and TM proteins are glycosylated at multiple sites. However, in some viruses, exemplified by MLV, TM is not glycosylated.

Although the SU and TM proteins are not always required for the assembly of enveloped virion particles as such, they do play an essential role in the entry process. In this regard, the SU domain binds to a receptor molecule—often a specific receptor molecule—on the target cell. It is believed that this binding event activates the membrane fusion-inducing potential of the TM protein after which the viral and cell membranes fuse. In some viruses, notably MLV, a cleavage event—resulting in the removal of a short portion of the cytoplasmic tail of TM—is thought to play a key role in uncovering the full fusion activity of the protein (Brody et at 1994 J. Virol. 68: 4620-4627, Rein et at 1994 J. Virol. 68: 1773-1781). This cytoplasmic"tail", distal to the membrane-spanning segment of TM remains on the internal side of the viral membrane and it varies considerably in length in different retroviruses.

Thus, the specificity of the SU/receptor interaction can define the host range and tissue tropism of a retrovirus. In some cases, this specificity may restrict the transduction potential of a recombinant retroviral vector. Here, transduction includes a process of using a viral vector to deliver a non-viral gene to a target cell. For this reason, many gene therapy experiments have used MLV. A particular MLV that has an envelope protein called 4070A is known as an amphotropic virus, and this can also infect human cells because its envelope protein "docks" with a phosphate transport protein that is conserved between man and mouse. This transporter is ubiquitous and so these viruses are capable of infecting many cell types. In some cases however, it may be beneficial, especially from a safety point of view, to specifically target restricted cells. To this end, several groups have engineered a mouse ecotropic retrovirus, which unlike its amphotropic relative normally only infects mouse cells, to specifically infect particular human cells. Replacement of a fragment of an envelope protein with an erythropoietin segment produced a recombinant retrovirus which then bound specifically to human cells that expressed the erythropoietin receptor on their surface, such as red blood cell precursors (Maulik and Patel 1997 "Molecular Biotechnology: Therapeutic Applications and Strategies" 1997. Wiley-Liss Inc. pp 45.).

In addition to gag, pol and env, the complex retroviruses also contain "accessory" genes which code for accessory or auxillary proteins. Accessory or auxillary proteins are defined as those proteins encoded by the accessory genes in addition to those encoded by the usual replicative or structural genes, gag, pol and env. These accessory proteins are distinct from those involved in the regulation of gene expression, like those encoded by tat, rev, tax and rex. Examples of accessory genes include one or more of vif, vpr, vpx, vpu and nef. These accessory genes can be found in, for example, HIV (see, for example pages 802 and 803 of "Retroviruses" Ed. Coffin et at Pub. CSHL 1997). Non-essential accessory proteins may function in specialised cell types, providing functions that are at least in part duplicative of a function provided by a cellular protein. Typically, the accessory genes are located between pol and env, just downstream from env including the U3 region of the LTR or overlapping portions of the env and each other.

The complex retroviruses have evolved regulatory mechanisms that employ virally encoded transcriptional activators as well as cellular transcriptional factors. These trans-acting viral proteins serve as activators of RNA transcription directed by the LTRs. The transcriptional trans-activators of the lentiviruses are encoded by the viral tat genes. Tat binds to a stable, stem-loop, RNA secondary structure, referred to as TAR, one function of which is to apparently optimally position Tat to trans-activate transcription.

As mentioned earlier, retroviruses have been proposed as a delivery system (other wise expressed as a delivery vehicle or delivery vector) for inter alia the transfer of a NOI, or a plurality of NOIs, to one or more sites of interest. The transfer can occur in vitro, ex vivo, in vivo, or combinations thereof. When used in this fashion, the retroviruses are typically called retroviral vectors or recombinant retroviral vectors. Retroviral vectors have even been exploited to study various aspects of the retrovirus life cycle, including receptor usage, reverse transcription and RNA packaging (reviewed by Miller, 1992 Curr Top Microbiol Immunol 158: 1-24).

In a typical recombinant retroviral vector for use in gene therapy, at least part of one or more of the gag, pol and env protein coding regions may be removed from the virus. This makes the retroviral vector replication-defective. The removed portions may even be replaced by a NOI in order to generate a virus capable of integrating its genome into a host genome but wherein the modified viral genome is unable to propagate itself due to a lack of structural proteins. When integrated in the host genome, expression of the NOI occurs—resulting in, for example, a therapeutic effect. Thus, the transfer of a NOI into a site of interest is typically achieved by: integrating the NOI into the recombinant viral vector; packaging the modified viral vector into a virion coat; and allowing transduction of a site of interest—such as a targeted cell or a targeted cell population.

It is possible to propagate and isolate quantities of retroviral vectors (e.g. to prepare suitable titres of the retroviral vector) for subsequent transduction of, for example, a site of interest by using a combination of a packaging or helper cell line and a recombinant vector.

In some instances, propagation and isolation may entail isolation of the retroviral gag, pol and env genes and their separate introduction into a host cell to produce a "packaging cell line". The packaging cell line produces the proteins required for packaging retroviral DNA but it cannot bring about encapsidation due to the lack of a psi region. However, when a recombinant vector carrying a NOI and a psi region is introduced into the packaging cell line, the helper proteins can package the psi-positive recombinant vector to produce the recombinant virus stock. This can be used to infect cells to introduce the NOI into the genome of the cells. The recombinant virus whose genome lacks all genes required to make viral proteins can infect only once and cannot propagate. Hence, the NOI is introduced into the host cell genome without the generation of potentially harmful retrovirus. A summary of the available packaging lines is presented in "Retroviruses" (1997 Cold Spring Harbour Laboratory Press Eds: J M Coffin, S M Hughes, H E Varmus pp 449). However, this technique can be problematic in the sense that the titre levels are not always at a satisfactory level. Nevertheless, the design of retroviral packaging cell lines has evolved to address the problem of inter alia the spontaneous production of helper virus that was frequently encountered with early designs. As recombination is greatly facilitated by homology, reducing or eliminating homology between the genomes of the vector and the helper has reduced the problem of helper virus production.

More recently, packaging cells have been developed in which the gag, pol and env viral coding regions are carried on separate expression plasmids that are independently transfected into a packaging cell line so that three recombinant events are required for wild type viral production. This strategy is sometimes referred to as the three plasmid transfection method (Soneoka et at 1995 Nucl. Acids Res. 23: 628-633).

Transient transfection can also be used to measure vector production when vectors are being developed. In this regard, transient transfection avoids the longer time required to generate stable vector-producing cell lines and is used if the vector or retroviral packaging components are toxic to cells. Components typically used to generate retroviral vectors include a plasmid encoding the Gag/Pol proteins, a plasmid encoding the Env protein and a plasmid containing a NOI. Vector production involves transient transfection of one or more of these components into cells containing the other required components. If the vector encodes toxic genes or genes that interfere with the replication of the host cell, such as inhibitors of the cell cycle or genes that induce apoptosis, it may be difficult to generate stable vector-producing cell lines, but transient transfection can be used to produce the vector before the cells die. Also, cell lines have been developed using transient infection that produce vector titre levels that are comparable to the levels obtained from stable vector-producing cell lines (Pear et at 1993, PNAS 90: 8392-8396).

In view of the toxicity of some HIV proteins—which can make it difficult to generate stable HIV-based packaging cells—HIV vectors are usually made by transient transfection of vector and helper virus. Some workers have even replaced the HIV Env protein with that of vesicular stomatis virus (VSV). Insertion of the Env protein of VSV facilitates vector concentration as HIV/VSV-G vectors with titres of $5\times10^5$ ($10^8$ after concentration) were generated by transient transfection (Naldini et at 1996 Science 272: 263-267). Thus, transient transfection of HIV vectors may provide a useful strategy for the generation of high titre vectors (Yee et al 1994 PNAS. 91: 9564-9568).

If the retroviral component includes an env nucleotide sequence, then all or part of that sequence can be optionally replaced with all or part of another env nucleotide sequence. Replacement of the env gene with a heterologous env gene is an example of a technique or strategy called pseudotyping. Pseudotyping is not a new phenomenon and examples may be found in WO-A-98/05759, WO-A-98/05754, WO-A-97/17457, WO-A-96/09400, WO-A-91/00047 and Mebatsion et at 1997 Cell 90,841-847.

Pseudotyping can confer one or more advantages. For example, with the lentiviral vectors, the env gene product of the HIV based vectors would restrict these vectors to infecting only cells that express a protein called CD4. But if the env gene in these vectors has been substituted with env sequences from other RNA viruses, then they may have a broader infectious spectrum (Verma and Somia 1997 Nature 389: 239-242). By way of example—workers have pseudotyped an HIV based vector with the glycoprotein from VSV (Verma and Somia 1997 ibid). Alternatively, env can be modified so as to affect (such as to alter) its specificity.

Thus, the term "recombinant retroviral vector" describes an entity (such as a DNA molecule) which contains sufficient retroviral sequences to allow an RNA transcript of the vector to be packaged in the presence of essential retroviral proteins into a retroviral particle capable of infecting a target cell. Infection of the target cell includes reverse transcription and integration into the target cell genome.

The term "recombinant retroviral vector" also covers a retroviral particle containing an RNA genome encoded by the DNA molecule. The retroviral vector will also contain non-viral genes which are to be delivered by the vector to the target cell. A recombinant retroviral vector is incapable of independent replication to produce infectious retroviral particles. Usually, a recombinant retroviral vector lacks functional gag-pol and/or env genes, or other genes encoding proteins essential for replication.

The term "targeted retroviral vector" means a recombinant retroviral vector whose ability to infect a cell or to be expressed in the target cell is restricted to certain cell types within the host organism. An example of targeted retroviral vectors is one with a genetically modified envelope protein which binds to cell surface molecules found only on a limited number of cell types in the host organism. Another example of a targeted retroviral vector is one which contains promoter and/or enhancer elements which permit expression of one or more retroviral transcripts in only a proportion of the cell types of the host organism.

Thus, the present invention provides a useful delivery system. The delivery system is capable of targeting an NOI and/or a POI to a tumour—i.e. capable of homing a NOI and/or POI in on a tumour.

The vector may be used to administered directly to an entity—such as an organism or a cell thereof—such as ex vivo or in vivo. In this sense the vector may be delivered directly, for example, to a tumour site. Alternatively, the vector may be administered to an entity by way of a carrier—such as ex vivo or in vivo. An example of a carrier would be a liposome or a cell in which would be contained the vector. An example of a suitable carrier cell would be a haematpoietic cell, such as a myeloid cell. These carrier cells may increase the further specificity of the vector of the present invention.

These and other aspects of the present invention will now be elaborated on further.

The perceived potential of monoclonal antibody-based therapies for treatment of neoplastic disease has not been fully realised (reviewed in Scheinberg and Chapman 1995, In Monoclonal antibodies (ed. Birch and Lennox) Chapter 2.1; George et al., 1994 Immunol. Today 15; 559-561). Consequently, monoclonal antibodies have been conjugated to radioisotopes, cytotoxic drugs or toxins in an attempt to improve efficacy. However, clinical trials with such conjugates have generally led to disappointing results. One of the principal reasons for the lack of efficacy of antibodies and antibody conjugates in the treatment of solid tumours is the poor penetration of solid tumours by immunoglobulins and other proteins such as immunotoxins of high molecular weight (e.g. Juweid et al. 1992, Cancer Res. 52; 5144-5153; Epenetos et al. 1986 Cancer Res. 46; 3183-3191). Other reasons for lack of efficacy include the non-specific toxicity, immunogenicity and inappropriate pharmacokinetics of many immunotoxins and antibody-radionuclide conjugates introduced into the systemic circulation (reviewed in Scheinberg and Chapman 1995. In Monoclonal antibodies (ed. Birch and Lennox) Chapter 2.1).

In contrast to the general lack of in vivo efficacy, many monoclonal antibodies show pronounced ability to inhibit the growth of tumour cells in certain in vitro assays (reviewed in Sandlie and Michaelsen 1996 In Antibody engineering: a practical approach. Ed McCafferty et at Chapter 9). It is well established that binding of specific antigen by an antibody can lead to activation of a variety of effector functions mediated via the Fc portion of the antibody heavy chain. The Fc regions of different immunoglobulin classes mediate different effector functions, including activation of complement cascades and binding to Fc receptors on various immune effector cells (Duncan et at 1988 Nature 332; 563 and 738). In in vitro assays, engagement of Fc receptors present on immune effector cells by antibody bound to tumour target cells can lead to destruction of the target cell by a variety of mechanisms collectively termed antibody dependent cellular cytotoxicity (ADCC). For example engagement of Fc-receptors for IgG, on human monocytes and macrophages, neutrophils and natural killer (NK) cells by antibodies of the IgG1 and IgG3 and to a much lesser extent IgG2 and IgG4 subclasses, stimulates ADCC (Munn et at 1991 Cancer Res. 51; 1117-1123; Primus et al., 1993 Cancer Res. 53; 3355-3361). However, the relatively poor ability of such antibodies to destroy tumours in vivo suggests that ADCC does not play a significant role in many of the current antibody-based therapies (George et al, 1994 Immunol. Today 15; 559-561). There are several possible reasons for this, including the poor penetration of antibodies into solid tumours (Yuan et al. 1995 Cancer Res. 55; 3752-3756) and the fact that the majority of the high-affinity receptor (FcgRI) molecules present on macrophages are normally occupied by serum IgG which will be poorly competed by specific antibody (Munn et al 1991 Cancer Res. 51; 1117-1123).

It has previously been shown that tumour cells transduced with genes encoding monoclonal antibodies can participate in ADCC reactions mediated by xenogeneic NK cells in vitro (Primus et al. 1993 Cancer Res. 53: 3355-3361). However, NK cells play little role in the destruction of tumour cells in vivo, in part because their killing functions are inhibited by the presence of self MHC Class I on autologous tumour cells (Correa and Raulet 1995 Immunity 2; 61-71).

It has also been postulated that tumour infiltrating lymphocytes (TILs) could be used as a vehicle to deliver antibody genes to a tumour to secrete anti-tumour antibodies at the tumour site (Tsang et at 1993 J. Immunother. 13; 143-152.) However, ex vivo transduction of TILs followed by autologous transplantation using marker genes has shown that isolated TILs show no specific homing mechanism which could allow them to return to tumour deposits (Economou et at 1996 J. Clin. Invest. 97; 515-521) and so any such approach is of limited value. The present invention is in contrast to these findings since there is provided a vector that can target or deliver an NOI and/or a POI to a tumour mass (or site).

Transduction of a gene encoding a single-chain immunotoxin into human lymphokine-activated T-cells (LAK cells) has also been reported (Chen et at 1997 Nature 385,78-80). In addition to the problems of re-introducing the LAK cells to the site of the tumour, such an approach also suffers from the potential drawbacks associated with being restricted to ex vivo use. These include the necessity of culturing the T-cells in high levels of a cytokine such as IL-2 to generate LAK cells with consequent problems in generating sufficient cells for therapy.

In one aspect, the present invention relates to the use of genetic vectors to deliver genes (such as therapeutic genes) encoding secreted tumour binding proteins (TBPs) to the interior of a tumour mass and identifies ways to target expression of TBPs to the interior of the tumour. Expression of the gene or genes encoding the TBP within the tumour mass then leads to local production of TBP with consequent reduction of tumor growth, survival or dissemination by a variety of mechanisms. Because the TBP is secreted, TBP produced by transduced cells can act not only on the transduced cell but on neighbouring tumour cells as well and hence achieve a bystander effect.

There are a number of cell types present within a tumor mass in addition to the cancerous cells. These can include cells of the tumour vasculature (e.g. endothelial cells) and immune cells which infiltrate the tumour, such as tumour-infiltrating lymphocytes (TIL) and macrophages (Normann 1985 Cancer Metastasis Re. 4: 277-291; Leek et at 1996 Cancer Res. 56: 4625-4629). Any of these cell types can be targeted for expression of the TBP and can serve as a local factory within the tumour for production of TBP. Preferably, the cells in the tumour mass which are used to produce the TBP are the cancerous cells, endothelial cells or macrophages. Alternatively, the progenitors of monocytes or endothelial cells may be targeted, such as CD34-positive peripheral blood mononuclear cells (Asahara et al. 1997 Science 275: 964-967).

Preferably, the TBP comprises one or more binding domains capable of binding to one or more TACSMs which are present on the cancerous cells. Thus the TBP, produced from one or more of the cell types within the tumour mass is secreted and is directed to the cancerous cells by its affinity for the TACSM. The TACSM may be selectively present on a restricted number of cell types. Thus the amount of TACSM present on the majority of the cancerous cells within the tumour mass is higher than on surrounding tissues. Preferably, the TACSM is detectably present only on tumour cells and a limited number of other tissue types in the individual containing the tumour. More preferably, the TACSM is essentially tumour-specific in the individual containing the tumour.

The one or more binding domains of the TBP may consist of, for example, a natural ligand for a TACSM, which natural ligand may be an adhesion molecule or a growth-factor receptor ligand (e.g. epidermal growth factor), or a fragment of a natural ligand which retains binding affinity for the TACSM. Alternatively, the binding domains may be derived from heavy and light chain sequences from an immunoglobulin (Ig) variable region. Such a variable region may be derived from a natural human antibody or an antibody from another species such as a rodent antibody. Alternatively the variable region may be derived from an engineered antibody such as a humanised antibody or from a phage display library from an immunised or a non-immunised animal or a mutagenised phage-display library. As a second alternative, the variable region may be derived from a single-chain variable fragment (scFv). The TBP may contain other sequences to achieve multimerisation or to act as spacers between the binding domains or which result from the insertion of restriction sites in the genes encoding the TBP, including Ig hinge sequences or novel spacers and engineered linker sequences.

The TBP may comprise, in addition to one or more immunoglobulin variable regions, all or part of an Ig heavy chain constant region and so may comprise a natural whole Ig, an engineered Ig, an engineered Ig-like molecule, a single-chain Ig or a single-chain Ig-like molecule. Alternatively, or in addition, the TBP may contain one or more domains from another protein such as a toxin.

In one aspect of the invention, there is provided a gene delivery system for targeting one or more genes encoding a TBP to a tumour, comprising a genetic vector encoding a TBP and an in vivo gene-delivery system. The gene delivery system may be a non-viral gene delivery system such as DNA compacted with a DNA-compaction agent, or a liposome or immunoliposome which may contain DNA compacted with a DNA-compaction agent (such as a poly-lysine). The vector may be a plasmid DNA vector. Alternatively the vector may be a recombinant viral vector such as an adenovirus vector, an adeno-associated virus (AAV) vector, a herpes-virus vector or a retroviral vector in which case gene delivery is mediated by viral infection of a target cell. Preferably the vector is a recombinant retroviral vector, which may be a targeted retroviral vector. Preferably, the retroviral vector is resistant to human complement, for example by production in a human cell line.

Typically, the vector will contain a promoter to direct expression of the or each gene (such as a therapeutic gene) and may contain additional genetic elements for the efficient or regulated expression of TBP genes, including enhancers, translation initiation signals, internal ribosome entry sites (IRES), splicing and polyadenylation signals. The promoter and/or enhancer may be tissue-restricted in its activity. For example a tumour-specific promoter-enhancer, such as a 5T4 antigen gene promoter-enhancer or the CEA-gene promoter-enhancer may be used. Alternatively, or additionally, an element or elements for regulated expression may be present, such as a hypoxia regulated enhancer. An example of a hypoxia regulated expression element (HRE) is a binding element for the transcription factor HIF1. The enhancer elements or elements conferring regulated expression may be present in multiple copies. Preferably, expression of the or a gene (such as a therapeutic gene) is inducible by hypoxia (or low oxygen supply) such as may be found in a tumour mass. Most preferably, the promoter and/or enhancer directing expression of the gene (such as a therapeutic gene) contains both hypoxia-responsive elements and elements which give higher expression in tumour cells than in neighbouring non-tumour cells.

Additional vector components will be provided for other aspects of vector function such as vector maintenance, nuclear localisation, replication, and integration as appropriate using components which are well known in the art.

In a preferred embodiment of this aspect of the invention, a retroviral vector is provided for in vivo delivery of the gene or genes encoding the TBP to the tumour. Suitable retroviral vectors are known in the art (see for example Gunzberg and Salmons 1996 In Gene Therapy ed. Lemoine and Cooper.

Bios; and Cosset et al. 1995 J. Virol. 69; 7430-7436). In a particularly preferred embodiment, expression of the TBP may be enhanced in the hypoxic regions of the tumour by the inclusion of hypoxia regulated genetic elements in the retroviral vector. In this case, the hypoxia-regulated elements may be inserted into one or both of the retroviral LTRs in place of the LTR enhancer or in another position in the vector, by standard molecular biology techniques. The gene or genes encoding the TBP may be expressed from a promoter-enhancer which leads to enhanced expression in the tumour cells compared with neighbouring non-tumour cells or is preferably essentially tumour-specific. Examples of suitable promoters include the promoter-enhancer of the gene for 5T4 antigen, the promoter-enhancer of the MUC1 gene or the CEA gene.

In an other aspect of the invention there is provided a method of treating cancer comprising administering the TBP gene or genes in a gene delivery system of the first aspect of the invention either systemically or directly to the site of a tumour.

In an other aspect of the invention, is provided a gene delivery system for introducing one or more genes encoding a TBP into cells of the haematopoietic (preferably myeloid haematopoietic) cell lineage either in vivo or ex vivo. Preferably the haematopoietic (preferably myeloid haematopoietic) cells are of the monocyte-macrophage lineage or a precursor of such cells such as a CD34-positive stem cell. For ex vivo delivery, the genes can be inserted into a plasmid vector and delivered by one of a variety of DNA transfection methods including electroporation, DNA biolistics, lipid-mediated transfection or compacted DNA-mediated transfection. Alternatively a viral vector can be used to transduce haematopoietic (preferably myeloid haematopoietic) cells or CD34-positive stem cells ex vivo, such as an adenovirus vector, a retroviral vector or a lentiviral vector. The vector will contain a promoter to direct expression of the or each gene (such as a therapeutic gene) and may contain additional genetic elements for efficient or regulated expression including enhancers, translation initiation signals, internal ribosome entry sites (IRES), splicing and polyadenylation signals. The promoter, or an enhancer or splicing signals may be tissue-restricted and preferentially active in mononuclear phagocytes such as macrophages. The promoter and/or enhancer may contain elements for regulated expression such as a hypoxia-regulated enhancer. An example of a hypoxia regulated expression element is HIF1 transcription factor response element. Such an element may be present in multiple copies. Examples of hypoxia-regulated promoters and enhancers include those from the enolase gene, the erythropoietin gene, and genes encoding glycolytic enzymes (Semenza et al., 1994 J. Biol. Chem 269; 23757-23763) such as the PGK gene. Isolated HREs can be multimerised in order to increase the response to hypoxia. Additional vector components may be provided for other aspects of vector function such as vector maintenance, nuclear localisation, replication and integration as appropriate using components which are well known in the art.

After introduction of the vector into the cells ex vivo, the cells can be re-introduced into the patient directly or they can be stimulated to differentiate along the monocyte-macrophage differentiation pathway using appropriate combinations of cytokines and growth factors prior to re-introduction into the patient. CD34-positive cells are stimulated to differentiate using cytokines including IL-3, GMCSF and MCSF. Monocytes are differentiated either by culture attached to plastic or using GMCSF either alone or in combination with other cytokines including MCSF.

For introduction of genes (such as therapeutic genes) into haematopoietic (preferably myeloid haematopoietic) cells or CD34-positive stem cells in vivo, a suitable in vivo delivery system can be used to deliver the transcription units described above. The gene delivery system may be a non-viral gene delivery system such as DNA compacted with a DNA-compaction agent, or a liposome or immunoliposome which may contain DNA compacted with a DNA-compaction agent. Alternatively the vector may be a recombinant viral vector such as a targeted adenovirus vector, an adeno-associated viral (AAV) vector, a herpes-virus vector or a retroviral vector such as a lentiviral vector. Preferably the vector is a targeted recombinant retroviral vector, which is preferably resistant to human complement, for example by preparation of the vector from a human packaging cell line.

CD34-positive stem cells can also differentiate to form endothelial cells (Ashara et al. 1997 Science 275; 964-967). Such a route of differentiation for CD34 positive stem cells containing TBP encoding genes according to the invention is envisaged in addition to differentiation to form monocytes and macrophages.

Additional vector components may be provided for other aspects of vector function such as vector maintenance, nuclear localisation, replication, and integration as appropriate using components which are well known in the art.

In a preferred embodiment of this aspect of the invention, a plasmid vector or a retroviral vector carrying a gene encoding a TBP under the control of a hypoxia regulated promoter or a promoter preferentially active in macrophages is introduced into autologous peripheral blood monocytes. The transfected monocytes are re-introduced into the patient where they migrate to the hypoxic regions of tumours permitting enhanced production of the TBP in the interior of the tumour mass. The macrophages are optionally treated with cytokines prior to re-injection into the patient. Alternatively or additionally the vector may include DNA sequences capable of expressing a cytokine gene such as a gene for IFNg, CSF-1 or GM-CSF in order to elicit the differentiation of the transfected cells. The cytokine gene may also be regulated by genetic elements which show enhanced activity at the site of the tumour.

In an other aspect of the invention, there is provided a method for treating cancer in a human or non-human mammal, comprising withdrawing an amount of blood from an individual suffering from cancer, preparing from the blood a cell preparation enriched in monocytes and macrophages or their stem-cell progenitors, introducing TBP genes into the cell preparation using a gene delivery system of the third aspect of the invention so as to bring about transfection or transduction of the monocytes and macrophages, or their stem-cell progenitors with the TBP genes, and re-introducing the transfected or transduced cells either systemically or directly to the site of the tumour. The cell preparations may optionally be treated with cytokines prior to reintroduction in order to elicit differentiation towards active macrophages.

In an other aspect of the invention is provided a method for treating cancer in a mammal, comprising administering to an individual a gene delivery system of the invention capable of expressing a TBP in cells derived from a haematopoietic (preferably myeloid haematopoietic) origin.

In a further aspect of the invention there is provided a genetic vector comprising a gene (such a therapeutic gene) or genes encoding a TBP, operably linked to an expression regulatory element selectively functional in a cell type present within a tumour mass. The TBP in this aspect of the invention inhibits tumour function by binding to a TACSM having an essential role in tumour cell survival or dissemination. The TACSM in this aspect of the invention may be a cell surface molecule which has a role in tumour cell growth, migration or metastasis, and is present on cancerous cells or on another cell type within the tumour mass. Preferably the TACSM is present on cancerous cells or tumour vasculature or on macrophages and is a molecule such as a growth-factor receptor, a plasminogen activator, a metalloproteinase or the 5T4 antigen. The gene or genes encoding the TBP may be delivered to the interior of the tumour by any of the routes described in the above two aspects of the invention. Binding of the TBP to the corresponding TACSM blocks the function of the TACSM and thereby leads to inhibition of growth, migration or metastasis of the tumour.

In a yet further aspect of the invention, a genetic vector comprising a gene (such as a therapeutic gene or genes) is delivered to the interior of the tumour wherein the gene (such as a therapeutic gene) encodes a TBP, which additionally contains one or more effector domains. The effector domain or domains may be activated on binding of the TBP to a TACSM leading to inhibition of tumour cell proliferation, survival or dissemination. The TACSM in this aspect of the invention is a cell surface molecule for which a specific TBP is available such as a tumour specific carbohydrate moiety, an oncofoetal antigen, a mucin, a growth-factor receptor or another glycoprotein. The TACSM is preferably an antigen restricted in its tissue distribution and found predominantly on the tumour cells and on the majority of cells within the tumour. Alternatively, the TACSM is present on tumour macrophages or the tumour vasculature. In some instances, the TACSM is not shed from the cell surface into the circulation to an appreciable extent. However, shedding may occur. By way of example, shedding of the 5T4 antigen into the stroma can serve to further localise the NOI and/or the POI to the tumour environment. The effector domain of the present invention may possess enzymatic activity and may be for example a pro-drug activating enzyme, or it may be a non-enzyme domain. Examples of TBPs containing effector domains with enzyme activity include antibody-enzyme conjugates or fusions. Antibody-enzyme conjugates have been described including conjugates with alkaline phosphatase (Senter et al., 1988 Proc. Natl. Acad. Sci. 85: 48424846); carboxypeptidase G2 (Bagshawe et al. 1988 Br. J. Cancer 58: 700703); P-lactamase (Shepherd et at 1991 Bioorg. Med. Chem. Left. 1: 21-26); and Penicillin-V-amidase (Kerr et al. 1990 Cancer Immunol. Immunother. 31: 202-206. Antibody-enzyme fusions have also been described (Goshorn et at 1993 Cancer Res 53: 2123-2127; Wels et al 1992 Bio/Technology 10: 1 1 28-1132). Each of these examples can be used in this aspect of the invention. Additional or alternative enzymes which may be included in TBPenzyme fusions include human Carboxypeptidase A1 or a mutant thereof (Smith et at 1997 J. Biol. Chem. 272: 15804-15816); cytosine deaminase (Mullen et al. 1994 Cancer Res. 54: 1503- 1506); HSV thymidine kinase (Borrelli et al. 1988 Proc. Natl. Acad. Sci. 85: 7572-7576.); nitroreductase; P450-Reductase and a P450.

Preferably the pro-drug activating enzyme domain or domains are genetically fused to the C-terminus of an immunoglobulin or immunoglobulin domain such as a scfv or a single-chain antibody or Fab-fragment. In a particularly preferred embodiment of this aspect of the invention, the immunoglobulin domain or domains are human or humanised and the enzyme is a human enzymp—such as a Carboxypeptidase a P450 or P450-Reductase. The enzyme may be a mutant enzyme which converts a pro-drug more efficiently than does the native human enzyme. In accordance with the present invention, any enzyme that has utility in an ADEPT strategy can be used.

In each case, a suitable pro-drug is used in the treatment of the patient in combination with the appropriate pro-drug activating enzyme. Examples of pro-drugs include etoposide phosphate (used with alkaline phosphatase Senter et al., 1988 Proc. Nat. Acad. Sci. 85: 4842-4846); 5-fluorocytosine (with Cytosine deaminase Mullen et al. 1994 Cancer Res. 54: 1503-1506); Doxorubicin-N-p-hydroxyphenoxyacetamide (with Penicillin-V-Amidase (Kerr et al. 1990 Cancer Immunol. lmmunother. 31: 202-206); Para-N-bis (2chloroethyl) aminobenzoyl glutamate (with Carboxypeptidase G2); Cephalosporin nitrogen mustard carbamates (with P-lactamase); SR4233 (with P450 Reducase); Ganciclovir (with HSV thymidine kinase, Borrelli et al. 1988 Proc. Natl. Acad. Sci. 85: 7572-7576) mustard pro- drugs with nitroreductase (Friedlos et al. 1997 J Med Chem 40: 1270-1275) and Cyclophosphamide (with P450 Chen et al. 1996 Cancer Res 56: 1331-1340).

Alternatively the effector domain may be a non-enzyme domain. Examples of non-enzyme effector domains include toxins such an exotoxin from a pseudomonad bacterium, all or part of a cytokine such as IL-2 or IFNγ, or effector domains from immunoglobulin heavy chains.

In a preferred embodiment of this aspect of the invention, the TBP contains an effector domain capable of activating macrophage FcgR I, II or III receptors. On binding of the TBP to antigen on the tumour cells, macrophages present within the hypoxic regions of the tumour are activated to destroy the tumour cells directly by phagocytosis or ADCC or are activated to secrete pro-inflammatory cytokines which serve to enhance the natural immunological response to the tumour. The TBP may contain an Fc region from an immunoglobulin, a mutant Fc region, a receptor-binding fragment of the Fc region or may contain another FcR-binding domain.

Preferably the TBP contains an entity, preferably an effector domain entity, that confers protein stability ex vivo and/or in vivo.

In accordance with the present invention, the TBP may include an intact Fc region from an IgG, (such as human IgG1 or IgG3), preferably from IgE (such as human IgGE), or a part thereof.

In one preferred embodiment of this aspect of the invention, the TBP is a Sab (single chain antibody) containing a human IgG1 constant region and a binding domain which recognises the 5T4 antigen.

In a particularly preferred embodiment of this aspect of the invention, the TBP is a Sab (single chain antibody) containing a human IgE constant region and a binding domain which recognises the 5T4 antigen.

The effector domain may be encoded by a portion of a cDNA fused in-frame to the DNA encoding the tumour-binding domain. Alternatively a genomic fragment containing introns may be used such as a human IgGI heavy chain constant region genomic fragment.

Here the term "intron" is used in its normal sense—e.g. an intervening sequence of DNA within a gene which is removed by RNA splicing and so is not present in the mature messenger RNA and does not code for protein. Introns can be conditional or alternatively spliced in different cell types.

Introduction of TBP-encoding genes into monocytes or macrophages may be combined with further treatments to elicit macrophage differentiation and activation. For example, cells maintained ex vivo may be treated with cytokines such as IFNγ, CSF-1 or GM-CSF prior to re-introduction into the patient. Alternatively, genes encoding these cytokines may be introduced into the monocytes/macrophages in the same or a different vector from the TBP genes in vivo or ex vivo. Consequently in a still further aspect of the invention there is provided a method of treating cancer in a mammal which comprises administering to an individual a combination of a cytokine or a cytokine-encoding gene and one or more TBP genes according to any of the previous aspects of the invention.

In accordance with the invention, standard molecular biology techniques may be used which are within the level of skill in the art. Such techniques are fully described in the literature. See for example; Sambrook et al. (1989) Molecular Cloning; a laboratory manual; Hames and Glover (1985-1997) DNA Cloning: a practical approach, Volumes I-IV (second edition). Methods for the engineering of immunoglobulin genes in particular are given in McCafferty et at (1996) Antibody engineering: a practical approach.

In a preferred aspect, the present invention relates to the delivery of TBP-encoding genes to the site of a tumour. This has considerable advantages for medical applications (such as therapeutic applications) in which TBPs are indicated since it circumvents a number of problems associated with delivery of proteins systemically in humans. In contrast to the problems associated with production and delivery of proteins, the methods of the invention allow the delivery of genes to the site of the tumour, thus circumventing a number of production problems. The TBPs are thereby produced in situ in the autologous human cells, which serve as a local factory for the production of the gene- based medicament (such as a therapeutic). This has significant advantages in minimising systemic toxicity. The activity of the protein is maximal since the glycosylation of the protein shows a human pattern appropriate to the individual being treated.

The methods of the invention can be used in conjunction with direct injection into the site of the tumour or systemic delivery of, for example targeted vectors or engineered haematopoietic (preferably myeloid haematopoietic) cells or their progenitors. Systemic delivery may be particularly advantageous in a number of indications, particularly in the treatment of disseminated disease. In these cases the gene delivery system or engineered cells can be administered intravenously by bolus injection or by infusion in a suitable formulation. A pharmaceutically acceptable formulation may include an isotonic saline solution, a buffered saline solution or a tissue-culture medium. Additional formulatory agents may be included such as preservative or stabilising agents.

Thus, the present invention also encompasses a pharmaceutical composition for treating one or more individuals by gene therapy, wherein the composition comprises a therapeutically effective amount of the vector according to the present invention or the expressed product thereof. The pharmaceutical composition may be for human or animal usage. Typically, a physician will determine the actual dosage which will be most suitable for an individual subject and it will vary with the age, weight and response of the particular patient.

The composition may optionally comprise a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder (s), lubricant (s), suspending agent (s), coating agent (s), solubilising agent (s), and other carrier agents that may aid or increase the viral entry into the target site (such as for example a lipid delivery system).

Where appropriate, the pharmaceutical compositions can be administered by any one or more of: inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intracavernosally, intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Thus, a preferred aspect of the present invention relates to a vector comprising (a) a NS coding for a TIP and (b) an NOI which encodes a POI; wherein the TIP is capable of recognising a tumour, such that in use the vector is capable of delivering the NOI and/or the POI to the tumour.

In one exemplary embodiment of the present invention TIP is IgG or IgE or a part thereof.

In another exemplary embodiment of the present invention, TIP is EGF or a part thereof.

In another exemplary embodiment of the present invention, TIP recognises a trophoblast cell surface antigen and at least one of the effector domains is a secreted co-stimulatory molecule. Further background teaching and details on this embodiment now follow.

The latter-mentioned aspect of the present invention relates to a process for the activation of lymphocytes and the use of activated lymphocytes in the treatment of cancer. It also relates to fusion proteins for the activation of lymphocytes, to nucleic acids encoding the fusion proteins and to vectors carrying the nucleic acids. Lymphocytes require at least two distinct signals in order to respond to antigens by activation of effector functions (Bretscher and Cohn 1970 Science 169: 1042-1049; Crabtree 1989 Science 243: 355-361). The primary signal is specific for antigen. For B-lymphocytes, the B-cell antigen receptor (surface immunoglobulin) recognises three-dimensional epitopes on a variety of macromolecules. For T-lymphocytes, the T-cell receptor (TCR) recognises peptide antigens displayed on the surface of antigen-presenting cells by proteins of the major histocompatability (MHC) family (Weiss et al. 1986 Ann Rev. Immunol. 4: 593-619).

Stimulation of the primary signal in isolation normally leads to apoptosis (programmed cell death) of the lymphocyte or leads to the establishment of a state of sustained unresponsiveness or anergy (Weiss et al. supra). In order to achieve activation of the lymphocyte, accessory signals are required which may be delivered by cytokines or by cell-surface co-stimulatory ligands present on antigen-presenting cells (APC).

There are a number of such co-stimulatory molecules now identified including adhesion molecules, LFA-3, ICAM-1, ICAM-2. Major co-stimulatory molecules present on APC are the members of the B7 family including B7-1 (CD80), B7-2 (CD86) and B7-3. These molecules are ligands of co-stimulatory receptors on lymphocytes including CD28 (WO92/00092), probably the most significant co-stimulatory receptor for resting T-cells. Different members of the B7 family of glycoproteins may deliver subtly different signals to T-cells (Nunes et al. 1996 J. Biol. Chem. 271: 1591-1598).

Established tumours, despite the fact that they commonly express unusual antigens on their surfaces, are poorly immunogenic. It has been postulated previously that one method for stimulating immune recognition of tumour cells would be to enhance antigen presentation and co-stimulation of lymphocytes in the context of tumour antigens. Transfection of the genes encoding B7-1 and B7-2, alone or in combination with cytokines, have been shown to enhance the development of immunity to experimental tumours in animal models (e.g. Leong et al. 1997 Int. J. Cancer 71: 476-482; Zitvogel et al. 1996 Eur. J. Immunol. 26: 1335-1341; Cayeux et al. 1997 J. Immunol 158: 2834-2841). However, in translating these results into a practical treatment for human cancer, there are a number of significant problems to be overcome. A major problem in such studies is the need to deliver B7 genes in vivo to a large number of cells of the tumour to achieve efficacy. A second problem is that it is important to target expression of B7 to the tumour cells to avoid inappropriate immune cell activation directed against other cell types.

This aspect of the present invention solves these specific problems by delivering a gene encoding a secreted co-stimulatory molecule ("SCM") with binding affinity for a tumour antigen. In this way, a relatively small number of transfected cells within the tumour act as a local factory to produce the co-stimulatory molecule which is shed from the producer cell and binds to other cells in the tumour. The aspect of the present invention has the additional advantage that tumour cells need not be the target for transfection.

The SCM of the invention is a novel engineered fusion protein comprising a signal peptide for secretion from mammalian cells, at least one antigen-binding domain from an immunoglobulin or an immunoglobulin-like molecule and at least one further domain which acts as a co-stimulatory signal to a cell of the immune system. The use of combinations of SCMs containing different co-stimulatory domains is also envisaged. The SCMs are produced by expression of SCM-encoding genes in the autologous cells of the individual to be treated and hence any post-translational modifications added to the protein by the host cell are authentic and provide fully functional protein and appropriate pharmacokinetics.

WO-A-92/00092 describes truncated forms of B7-1, derived by placing a translation stop codon before the transmembrane domain, secreted from mammalian cells. In that particular case, a heterologous signal peptide from the Oncostatin M gene was used. WO-A92/00092 also describes fusion proteins which contain the extracellular domain of B7-1 fused to the Fc region of an immunoglobulin. Such molecules can bind to CD28 on T-cells and serve to stimulate T-cell proliferation. However such stimulation occurs only to a moderate extent unless the B7 or B7-derivative is immobilised on a solid surface.

Gerstmayer et al. (1997 J. Immol. 158: 4584-4590) describes a fusion of B7-2 to an scFv specific for ErbB2 followed by a myc epitope tag and polyhistidine tag which is secreted when expressed in the yeast *Pichia pastoris*. This molecule retained binding for antigen and co-stimulated proliferation of T-cells prestimulated with PMA and IL-2. However, glycosylation of such a molecule is of the yeast type, which is likely to lead to inappropriate pharmacokinetics in humans.

In accordance with the present invention, any suitable co-stimulalatory domain(s) may be used. By way of example, co-stimulatory domains can be chosen from extracellular portions of the B7 family of cell-surface glycoproteins, including B7-1, B7-2 and B7-3 or other co-stimulatory cell surface glycoproteins such as but not limited to co-stimulatory receptor-ligand molecules including CD2/LFA-3, LFA-1/ICAM-1 and ICAM-3. Studies have demonstrated that T cell co-stimulation by monocytes is dependent on each of two receptor ligand pathways CD2/LFA-3 and LFA-1/ICAM-1 (Van Seventer et at 1991 Eur J Immunol 21: 1711-1718). In addition, it has been shown that ICAM-3, the third LFA-1 counterreceptor, is a co-stimulatory molecule for resting and activated T lymphocytes (Hernandez-Caselles et at 1993 Eur J Immunol 23: 2799-2806).

Other possible co-stimulatory molecules may include a novel glycoprotein receptor designated SLAM, has been identified which, when engaged, potentiates T-cell expansion in a CD28-independent manner and induces a ThO/Th1 cytokine production profile (Cocks et at 1995 Nature 376: 260-263).

CD6, a cell surface glycoprotein, has also been shown to function as a co-stimulatory and adhesion receptor on T cells. Four CD6 isoforms (CD6a, b, c, d) have been described (Kobarg et at 1997 Eur J Immunol 27: 2971-2980). A role for the very late antigen (VLA-4) integrin in the activation of human memory B cells has also been suggested (Silvy et at 1997 Eur J Immunol 27: 2757-2764). Endothelial cells also provide unique co-stimulatory signals that affect the phenotype of activated CD4+ T cells (Karmann et at 1996 Eur J Immunol 26: 610-617). A B3 protein, present on the surface of lipopolysaccharide-activated B cells, which can provide co-stimulation to resting T cells leading to a predominant release of interleukin (IL)-4 and IL-5 and negligible amounts of IL-2 and interferon gamma has been described (Vinay et at 1995 J Biol Chem 270: 23429-23436). The co-expression of a novel co-stimulatory T cell antigen (A6H) on T cells and tumour cells has suggested a possible function related to common properties of these cells (Labuda et at 1995 Int Immunol 7: 1425-1432).

In one preferred embodiment of the invention, the co-stimulatory domain is a portion of B7-1 or B7-2, more preferably the complete extracellular portion of B7-1 or B7-2.

The SCM is formed by expression of a novel gene encoding a fusion protein containing the antigen-binding domain or domains and the co-stimulatory domain or domains. If the antigen-binding domain is comprised of a heavy and a light chain, the co-stimulatory domain is fused to one or other of the immunoglobulin chains, preferably to the heavy chain. If the antigen-binding domain is a scFv, the co-stimulatory domain is fused to the scFv. The domains can be placed in the order (N-terminus to C-terminus): antigen-binding domain followed by co-stimulatory domain; or co-stimulatory domain followed by antigen-binding domain. Preferably, the co-stimulatory domain is placed at the N-terminus followed by the antigen-binding domain. A signal peptide is included at the N-terminus, and may be for example the natural signal peptide of the co-stimulatory extracellular domain. The different domains may be separated by additional sequences, which may result from the inclusion of convenient restriction-enzyme cleavage sites in the novel gene to facilitate its construction, or serve as a peptide spacer between the domains, or serve as a flexible peptide linker or provide another function. Preferably the domains are separated by a flexible linker.

Two or more different genes encoding different SCMs may be used to achieve improved co-stimulation, or both co-stimulation of naïve T-cells and induction of memory responses. For example a gene encoding an SCM containing the B7-1 extracellular domain may be administered with a gene encoding an SCM containing the B7-2 extracellular domain.

Thus in one aspect of the invention, there is provided one or more genetic vectors capable of expressing in mammalian cells one or more secreted co-stimulatory molecules, each secreted co-stimulatory molecule comprising at least one antigen-binding domain and at least one domain from the extracellular portion of a cell-surface co-stimulatory molecule. The co-stimulatory domain may be obtained from a molecule expressed on the surface of an antigen-presenting cell such as a B7 family member. Preferably the co-stimulatory domain is from B7-1, B7-2 or B7-3. Most preferably it is comprised of B7-1 amino acid residues 1 to approximately 215 of the mature B7-1 molecule (described in WO-A-96/00092) or amino acids 1 to approximately 225 of the mature cell-surface form of B7-2 (described in Gerstmeyer et al. 1997 J. Immunol. 158: 4584-4590).

The genetic vector according to this aspect of the invention comprises at least a promoter and enhancer for expression in mammalian cells and a polyadenylation site. Suitable promoters and enhancers include the MIE promoter-enhancer from human cytomegalovirus or promoters which are expressed preferentially in cells present within the tumour. Such promoter-enhancers include those from the MUC1 gene, the CEA gene or the 5T4 antigen gene. If two or more SCMs are expressed, the coding regions for these may be inserted into two separate vectors or a single vector may be used to express the two or more genes. In the latter case each gene is provided with a separate copy of the promoter, or an internal ribosome entry site (IRES) is used to separate the two coding sequences.

The present invention also covers the use of mutants, variants, homologues or fragments of the sequences disclosed herein.

The terms "variant", "homologue" or "fragment" in relation to the nucleotide sequences include any substitution of, variation of, modification of, replacement of, deletion of or addition of one (or more) nucleic acid from or to the sequence providing the resultant nucleotide sequence codes for or is capable of coding for an entity having the same function as that presented herein, preferably being at least as biologically active as the same. In particular, the term"homologue"covers homology with respect to structure and/or function providing the resultant nucleotide sequence codes for or is capable of coding for an entity having the same function as that presented herein. With respect to sequence homology, preferably there is at least 75%, more preferably at least 85%, more preferably at least 90% homology to the sequences shown herein. More preferably there is at least 95%, more preferably at least 98%, homology to the sequences shown herein.

In particular, the term "homology" as used herein may be equated with the term "identity". Relative sequence homology (i. e. sequence identity) can be determined by commercially available computer programs that can calculate % homology between two or more sequences. A typical example of such a computer program is CLUSTAL.

The terms "variant", "homologue" or "fragment" are synonymous with allelic variations of the sequences.

The term "variant" also encompasses sequences that are complementary to sequences that are capable of hybridising to the nucleotide sequences presented herein. Preferably, the term "variant"encompasses sequences that are complementary to sequences that are capable of hybridising under stringent conditions (e.g. 65° C. and 0.1×SSC {1×SSC=0.15 M NaCl, 0.015 $Na_3$ citrate pH 7.0}) to the nucleotide sequence presented herein.

The present invention also covers nucleotide sequences that can hybridise to the nucleotide sequences of the present invention (including complementary sequences of those presented herein). In a preferred aspect, the present invention covers nucleotide sequences that can hybridise to the nucleotide sequence of the present invention under stringent conditions (e.g. 65° C. and 0.1×SSC) to the nucleotide sequence presented herein (including complementary sequences of those presented herein).

The terms "variant", "homologue" or "fragment" in relation to the amino acid sequences include any substitution of, variation of, modification of, replacement of, deletion of or addition of one (or more) amino acid from or to the sequence providing the resultant amino acid sequence has the same function as that presented herein, preferably being at least as biologically active as the same. In particular, the term "homologue" covers homology with respect to structure and/or function providing the resultant amino acid sequence has the same function as that presented herein. With respect to sequence homology, preferably there is at least 75%, more preferably at least 85%, more preferably at least 90% homology to the sequences shown herein. More preferably there is at least 95%, more preferably at least 98%, homology to the sequences shown herein.

In summation, the present invention relates to a vector comprising (a) a NS coding for a TIP and optionally (b) an NOI which encodes a POI; wherein the TIP is capable of recognising a tumour, such that in use the vector is capable of delivering the NOI and/or the POI to the tumour.

A preferred aspect of the present invention relates to a vector comprising (a) a NS coding for a TIP and (b) an NOI which encodes a POI; wherein the TIP is capable of recognising a tumour, such that in use the vector is capable of delivering the NOI and/or the POI to the tumour.

A further preferred aspect of the present invention relates to a vector comprising (a) a NS coding for a TIP and (b) an NOI which encodes a POI; wherein the TIP is capable of recognising a tumour, such that in use the vector is capable of delivering the NOI and/or the POI to the tumour; and wherein the TIP and POI are fused to each other.

This aspect of the present invention is advantageous as it allows for the production and delivery of, for example, a fusion product that comprises an effector component and a targetting component.

A further preferred aspect of the present invention relates to a vector comprising (a) a NS coding for a TIP and (b) an NOI which encodes a POI; wherein the TIP is capable of recognising a tumour, such that in use the vector is capable of delivering the NOI and/or the POI to the tumour; wherein the TIP and POI are fused to each other; and wherein the POI is capable of being secreted.

This aspect of the present invention is highly advantageous as it provides a means for the in situ production of a POI by, for example, a small number of cells for the subsequent delivery of at least a portion of the produced POI to at least one neighbouring cell. Thus, one need only infect a small number of cells to achieve a beneficial therapeutic effect.

Thus, alternatively expressed, the present invention provides the use of a vector according to the present invention as an in situ production factory of any one or more of the NS, NOI, POI and TIP.

In addition, the present invention provides the use of a vector according to the present invention when present in a cell to deliver an NOI and/or POI to a neighbouring cell.

A more preferred aspect of the present invention relates to a vector comprising (a) a NS coding for a TIP, (b) an NOI which encodes a POI, and (c) a nucleotide sequence that codes for a secretory entity; wherein the TIP is capable of recognising a tumour, such that in use the vector is capable of delivering the NOI and/or the POI to the tumour; wherein the TIP and POI are fused to each other; and wherein the POI is capable of being secreted.

The invention will now be further described by way of examples, which are meant to serve to assist one of ordinary skill in the art in carrying out the invention and are not intended in any way to limit the scope of the invention. Reference is made to the following Figures:

FIG. 1*b*-1*d*—which shows the cDNA sequence encoding 5T4Sab1. The sequence begins with a HindIII restriction site followed by a translation initiation signal and a signal peptide.

FIG. 1*b*—which shows the cDNA sequence encoding 5T4Sab1. The sequence begins with a HindIII restriction site followed by a translation initiation signal and a signal peptide.

Figure 2C:
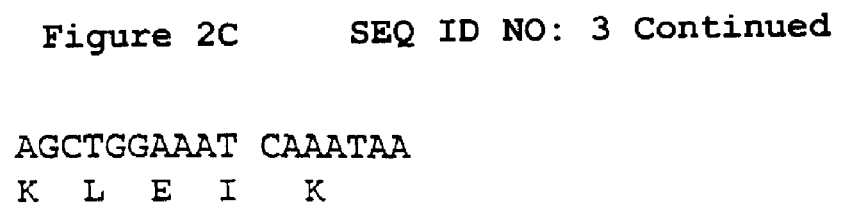

FIG. 2*a*-*c* shows the sequence of B7-1.5T4.1

Figure 3B:
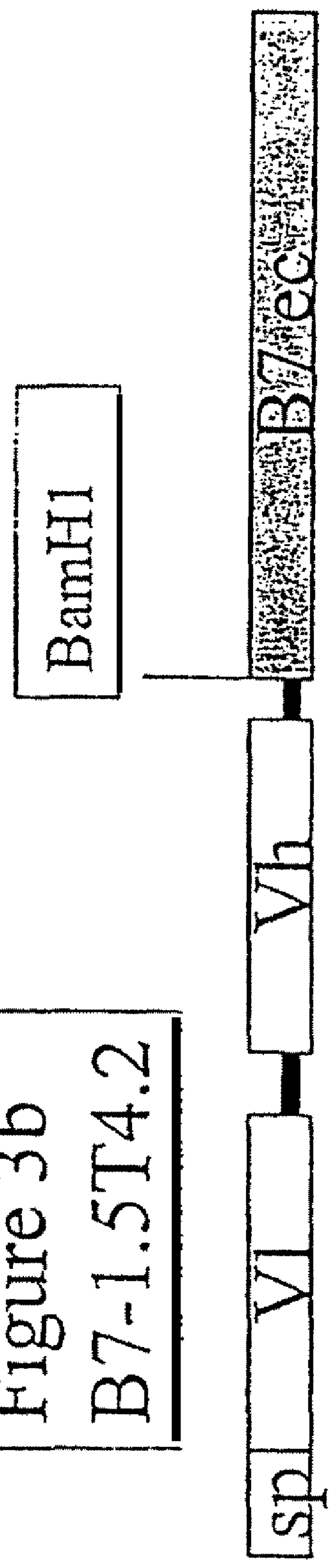

FIG. 3 shows a diagrammatic representation of two SCMs based on the B7-1 co-stimulatory domain; FIG. 3*a* shows the SCM B7-1.5T4.1 and FIG. 3*b* shows B7- 1.5T4.2 in which the order of the co-stimulatory and tumour-binding domains are reversed. Sp=signal peptide; B7 ec=extracellular domain of B7-1; V1=light chain variable domain of 5T4; Vh=heavy chain variable domain of 5T4.

FIG. 4*a*-*b* shows the sequences of the extracellular domain of human B7-2, including the signal peptide sequences. The mature protein begins at amino acid 17. The B7-2derived sequences is followed by a flexible linker gly-gly-gly-gly-ser (SEQ ID NO: 25).

FIG. 5 shows a simple, generic diagram (not to scale) of a retroviral genome including the elementary features of the LTRs, gag, pol, and env.

EXAMPLES

Example 1

Construction of 5T4 Sab and Retroviral-Vector Delivery to Tumour

The cDNA encoding the murine 5T4 monoclonal antibody is cloned and sequenced by standard techniques (Antibody engineering: a practical approach ed McCafferty et al. 1996 OUP). The sequence of the variable region of the antibody can be used to construct a variety of immunoglobulin-like molecules including scFvs. The coding sequence of a 5T4 scFv, 5T4scFv.1, is shown in FIG. 1*a*. In this molecule, the DNA sequence encodes the Vh from the mouse 5T4 monoclonal antibody followed by a 15 amino acid flexible linker and the V1 region of the mouse 5T4 antibody. The flexible linker encodes 3 copies of the amino-acid sequence gly-gly-gly-gly-ser (SEQ ID NO: 25) and the DNA sequence similarity between the repeats has been minimise to avoid the risk of recombination between the repeats when plasmids containing them are grown in *E. coli.*

The DNA sequence shown in FIG. 1*a* can also be used to construct a variety of single-chain antibodies (Sabs) by coupling scFv-encoding sequences to a sequence encoding a Fc region to form an in-frame fusion. A Sab is constructed using a series of DNA cassettes which can be independently varied to suit particular purposes.

Cassette 1-Translation Initiation Signal and Signal Peptide

In order to achieve correct translation initiation and secretion from mammalian cells, the following sequence is used:

```
                                          (SEQ ID NO: 23)
aagcttCCACCATGGGATGGAGCTGTATCATCCTCTTCTTGGTAGCA

ACAGCTACAGGTGTCCACTCC
```

This contains a convenient HindIII restriction site for cloning into expression vectors (lower case), the consensus translation initiation signal for mammalian cells (ANNATGPu) and the coding sequence for a signal peptide sequence from an immunoglobulin gene.

Cassette 2-scFv

The sequence of the secreted portion of the 5T4scFv.1 is shown in FIG. 1*a*. This molecule can be represented as Vh-(gly4-ser) 3 linker-V1.

5T4 scFv2 consists of the 5T4 variable region sequences connected in the order V1-flexible linker Vh. In this case the linker encodes the 20 amino-acid peptide four copies of the amino acid sequence gly-gly-gly-gly-ser (SEQ ID NO: 25). A longer linker improves assembly of the scFv when the V-region segments are in this order. (Pluckthun et at in Antibody Engineering: a practical approach, ed McCafferty et al. 1996 OUP).

Cassette 3-Heavy Chain Constant Region

The sequence of a human gl constant region genomic clone is given in Ellison et al. 1982 Nucl. Acids res. 10: 4071-4079. This sequence contains constant-region introns in addition to the coding sequence. This is fused in-frame to the 3'-end of one of the scFv sequences from Cassette 2. Vectors for convenient assembly of such constructs are described (Walls et al. 1993 Nucl. Acids Res. 21: 2921-2929.

A cDNA of a 5T4 Sab, designated 5T4Sab1 is shown in FIG. 1*b*, containing cassettes 1, 2 and 3.

For expression of a 5T4-specific scFv or Sab in human cells, the coding sequence is inserted into the vector pCIneo (Promega) under the control of a strong promoter and polyadenylation signal. The translation initiation signal and immunoglobulin leader (signal peptide) sequence from Cassette 1 at the 5'end of the coding region ensure efficient secretion of the scFv or Sab from mammalian cells.

For expression of an intact Ig, two separate translation cassettes are constructed, one for the heavy chain and one for the light chain. These are separated by an internal ribosome-entry site (IRES) from the picornavirus FMDV (Ramesh et al. 1996 Nucl. Acids Res. 24: 2697-2700. Alternatively, each cDNA is expressed from a separate copy of the hCMV promoter (Ward and Bebbington 1995 In Monoclonal Antibodies ed Birch and Lennox. Wiley-Liss).

For production of retrovirus capable of expressing 5T4 antibody or immunoglobulin-like molecules with 5T4 specificity, the gene encoding a 5T4-based Sab, or a dicistronic message encoding heavy and light chains, is inserted into a retroviral vector in which retroviral genomic transcripts are produced from a strong promoter such as the hCMV-MIE promoter. A suitable plasmid is pHIT111 (Soneoka et al. 1995 Nucl. Acids Res. 23; 628- 633) and the required gene is inserted in place of the LacZ gene using standard techniques. The resulting plasmid, pHIT-5T4.1 is then transfected into the FLYRD18 or FLYA13 packaging cell lines (Cosset et al. 1995 J. Virol. 69; 7430-7436) and transfectants selected for resistance to G418 at 1 mg/ml. G418-resistant packaging cells produce high titres of recombinant retrovirus capable of infecting human cells. The virus preparation is then used to infect human cancer cells and can be injected into tumours in vivo. The 5T4 Sab is then expressed and secreted from the tumour cells.

In pHIT111, the MoMLV LTR promoter-enhancer is used for expression of the therapeutic gene in the target cell. The vector can also be modified so that the therapeutic gene is transcribed from an internal promoter-enhancer such as one which is active predominantly in the tumour cells or one which contains a hypoxia regulated element. A suitable promoter is a truncated HSV TK promoter with 3 copies of the mouse PGK HRE (Firth et al. 1994 Proc. Natl. Acad. Sci. 91: 6496-6500).

Example 2

Transfection of Macrophages/Monocytes with an Expression Vector Encoding TBP

Peripheral blood mononuclear cells are isolated from human peripheral blood at laboratory scale by standard techniques procedures (Sandlie and Michaelsen 1996 In Antibody engineering: a practical approach. Ed McCafferty et al. Chapter 9) and at large scale by elutriation (e.g. Ceprate from CellPro). Adherent cells (essentially monocytes) are enriched by adherence to plastic overnight and cells can be allowed to differentiate along the macrophage differentiation pathway by culturing adherent cells for 1-3 weeks.

Monocytes and macrophages are transfected with an expression vector capable of expressing TBP in human cells. For constitutive high level expression, the TBP is expressed in a vector which utilises the hCMV-MIE promoter-enhancer, pCI (Promega). For hypoxia-induced expression, the hCMV promoter is replaced by a promoter containing at least one HRE. A suitable promoter is a truncated HSV TK promoter with 3 copies of the mouse PGK HRE (Firth et al. 1994 Proc. Natl. Acad. Sci. 91: 6496-6500).

A variety of transfection methods can be used to introduce vectors into monocytes and macrophages, including particle-mediated DNA delivery (biolistics), electroporation, cationic agent-mediated transfection (e.g. using Superfect, Qiagen). Each of these methods is carried out according to the manufacturer's instructions, taking into account the parameters to be varied to achieve optimal results as specified by the individual manufacturer. Alternatively, viral vectors may be used such as defective Adenovirus vectors (Microbix Inc. or Quantum Biotechnologies Inc.).

Example 3

Assay for ADCC Mediated by Macrophages

Cells from primary human tumours or tumour cell lines which have been transduced with retrovirus expressing TBP are mixed with autologous or heterologous human macrophages, prepared as described in Example 2, for analysis of ADCC activity mediated by the TBP. Alternatively, macrophages engineered to produce TBP as described in Example 2 can be used to direct ADCC on non-transduced tumour cells.

The assay is carried out according to standard procedures (Sandlie and Michaelsen 1996 In Antibody engineering: a practical approach. Ed McCafferty et al. Chapter 9) with appropriate modifications. Briefly, the effector cells (macrophages or freshly isolated monocytes) are suspended at $3\times10^6$ cells/ml in the appropriate tissue culture medium (DMEM/Hepes, obtained from Life Technologies, containing 1% Foetal Calf Serum). $3\times10^5$ tumour target cells, labelled with $^{51}Cr$ are placed in each well of a round-bottomed microtitre plate in 0.1 ml culture medium. (Note the culture medium can include spent medium from the cells producing the TBP). 50 ml effector cells are added to the wells, the plate is centrifuged at 300 g for 2 min and incubated at 37° C. for varying periods (e.g. 4 h) in a tissue culture incubator. The supernatant is then harvested by centrifugation and counted in a gamma counter. Results are expressed as percent lysis relative to total chromium release from an equivalent sample of target cells lysed with 0.1% Tween-20. The effector: target cell ratio can be varied in the assay to produce a titration curve.

For the prior stimulation of macrophage differentiation or priming, cytokines are added to the cultures. IFNg (Sigma) is added at between 100 and 5000 U/ml. CSF-1 or GM-CSF (Santa Cruz Biotechnology) can also be added at appropriate concentrations.

Example 4

Analysis of Efficacy in Animal Models

Human tumour-derived cell lines and tissues are cultured in vivo in genetically immunodeficient, "nude" mice according to well established techniques (see for example Strobel et al. 1997 Cancer Res. 57: 1228-1232; McLeod et al. 1997 Pancreas 14: 237- 248). Syngeneic mouse models, in which a syngeneic tumour line is introduced into an immunocompetent mouse strain may also be used. These serve as suitable animal models for evaluating gene delivery systems of the invention. Vectors or engineered cells are administered systemically or directly into the tumour and tumour growth is monitored in treated and untreated animals. This system is used to define the effective dose range of the treatments of the invention and the most appropriate route of administration.

Example 5

Construction of B7-scFv Fusion Proteins

The extracellular domain of B7-1 is defined by amino-acid residues 1-215 of the native human B7-1 protein. This sequence, together with its signal peptide-encoding sequence, is used to construct secreted fusion proteins which also contain the scFv derived from the 5T4 monoclonal antibody. The sequence of the 5T4 scFv is given in FIG. 1*a*.

A DNA coding sequence is constructed using standard molecular biology techniques which encodes a fusion protein in which the N-terminus of the 5T4 scFv is fused after amino acid 215 of human B7-1. The sequence of this coding sequence, B7-1.5T4.1, is shown in FIG. 2. The fusion protein contains a flexible (gly-gly-gly-gly-ser, SEQ ID NO: 25)) spacer between the B7-1 and 5T4 scFv sequences. The introduction of a convenient BamHI restriction site at the end of the linker insertion (beginning at nucleotide 733) also allows for further linkers to be screened for optimal expression of bi-functional fusion protein. FIG. 3 indicates the fusion protein in diagrammatic form. It is similarly possible to construct B7-1.5T4.2 (FIG. 3*b*) in which the scFv is N-terminal and the B7 extracellular domain is C-terminal. In this case only the coding sequence of the mature B7-1 (without signal peptide) is required. A signal peptide such as an immunoglobulin leader sequence is added to the N-terminus of the scFv in this instance.

For fusion proteins which use the co-stimulatory extracellular domain of B7-2, the signal peptide and extracellular domain of B7-2 is used in place of B7-1 sequences. FIG. 4 shows the coding sequence of the SCM B7-2.5T4. lco-stimulatory domain. It encodes the first 225 amino acids of human B7-2, preceded by its signal peptide, and a flexible linker gly-gly-gly-gly-ser, SEQ ID NO: 25. The BamHI site at the end of this sequence can be used to insert the domain upstream of the 5T4scFv. 1 (see FIG. 3). The sequence includes the B7-2 signal peptide which can serve to allow secretion of this fusion protein in which the B7-2 domain is at the N-terminus of the fusion protein.

Each engineered cDNA is inserted into the mammalian expression vector pCI to allow expression in mammalian tissue culture cells. For this purpose, a linker sequence is added to the 5'-end of the coding sequence which introduces a convenient restriction site for insertion into the polylinker of pCI and adds the translation initiation signal CCACC immediately adjacent to the first ATG codon. Constructs in pCI are transfected into a suitable mammalian host cell line such as COS-1 to confirm secretion of the SCM. The transcription cassette from pCI or an appropriate segment of the transcription cassette is subsequently sub-cloned into the expression vector to be used as the gene delivery system for therapeutic use.

Example 6

Transfection of Macrophages/Monocytes with an Expression Vector Encoding an SCM

Peripheral blood mononuclear cells are isolated from human peripheral blood at laboratory scale by standard techniques procedures (Sandlie and Michaelsen 1996 In Antibody engineering: a practical approach. Ed McCafferty et al. Chapter 9) and at large scale by elutriation (e.g. Ceprate from CellPro). Adherent cells (essentially monocytes) are enriched by adherence to plastic overnight and cells can be allowed to differentiate along the macrophage differentiation pathway by culturing adherent cells for 1-3 weeks.

Monocytes and macrophages are transfected with an expression vector capable of expressing SCM in human cells. For constitutive high level expression, the SCM is expressed in a vector which utilises the hCMV-MIE promoter-enhancer, pCI (Promega). For hypoxia-induced expression, the hCMV promoter is replaced by a promoter containing at least one HRE. A suitable promoter is a truncated HSV TK promoter with 3 copies of the mouse PGK HRE (Firth et al. 1994 Proc. Natl. Acad. Sci. 91: 6496-6500).

A variety of transfection methods can be used to introduce vectors into monocytes and macrophages, including particle-mediated DNA delivery (biolistics), electroporation, cationic agent-mediated transfection (e.g. using Superfect, Qiagen). Each of these methods is carried out according to the manufacturer's instructions, taking into account the parameters to be varied to achieve optimal results as specified by the individual manufacturer. Alternatively, viral vectors may be used such as defective Adenovirus vectors (Microbix Inc. or Quantum Biotechnologies Inc.).

Example 7

Analysis of SCM Binding to CTLA-4 and 5T4-Antigen Expressing Cells

The B7-1 or B7-2 domains are expected to bind specifically to CD28 and CTLA-4 present on human T-cells. Binding to T-cells or Chinese hamster ovary cells transfected with human CTLA-4 or CD28 is determined using FACS analysis as follows. $5\times10^5$ CTLA-4 expressing target cells or equivalent cells lacking CTLA-4 (untransfected CHO cells) are incubated with 0.1 ml culture supernatant from COS-1 cells transiently transfected with SCM genes for 1 h at 4° C. The cells are washed and incubate with 1 mg monoclonal antibody specific for the B7 domain (e.g. Mab 9E10) followed by FITC-labelled goat anti-mouse IgG (Pharmingen) and analysis by FACS.

Binding of scFv to 5T4-antigen is similarly assessed using target cells expressing 5T4- antigen (5T4-transfected A9 cells) or control cells (A9).

Example 8

Analysis of Co-Stimulatory Activity

An established mouse cell line of Balb/c origin such as HC11 cells is transfected with the cDNA encoding human 5T4-antigen (Myers et al. 1994 J. Biol. Chem. 269; 9319-9324) inserted in the expression vector pCIneo.

Splenic T-cells from Balb/c mice are isolated by standard procedures (Johnstone and Thorpe 1996 In Immunochemistry in Practice. Blackwell. Chapter 4). T-cells are pre-stimulated by incubation for 1-2 days in medium containing 10 ng/ml PMA (Sigma) and 100 U/ml human IL-2 (Boehringer Mannheim). HC11-5T4 cells are incubated at $10^4$ cells /well of a 96-well tissue culture tray for 2 h with up to 0.1 ml supernatant from COS cells transfected with SCM gene. Up to $10^5$ pre-stimulated T-cells are added to each well, the cells are pulsed with 0.25 mCi/well $^3$H-thymidine and incorporation of $^3$H-thymidine is measured using a liquid scintillation counter after 24 h.

Incorporation of $^3$H-thymidine is anticipated to be enhanced by the presence of SCM.

Example 9

Analysis of Co-Stimulation in Animal Models

HC11 cells transfected with the human 5T4-antigen gene (Example 4) are grown as tumours in Balb/c mice. SCM genes B7-1.5T4.1 or B7-2.5T4.1 or a combination of both genes are introduced into the tumour cells prior to implantation and the growth of the tumours and the growth of control tumours which do not express SCM genes in vivo are monitored.

It is believed that the expression of SCM genes lead to significant reduction in tumour growth.

Example 10

Construction of a B7-1/ScFv, Specific for Human 5T4, Fusion Protein

Standard molecular biology techniques are used to construct a fusion protein consisting of the leader sequence and extracellular domain of B7-1, fused via a flexible linker to the VH and VL of the murine Mab 5T4 specific to human 5T4.

The flexible linker, used to join the extracellular domain of B7.1 and the ScFv, was constructed by annealing two homologous oligonucleotides with engineered 5' Sma I and 3' Spe I sites-using oligonucleotides upper

```
                                        (SEQ ID NO: 24)
5' GGG GGT GGT GGG AGC GGT GGT GGC GGC AGT GGC

GGC GGC GGA A 3'
```

and lower

```
                                        (SEQ ID NO: 8)
5' CTA GTT CCG CCG CCG CCA CTG CCG CCA CCA CCG

CTC CCA CCA CCC CC 3'
```

The linker is cloned into pBluescript (Stratagene) via Sma I and Spe I to produce pLINK. The signal peptide (sp) and extracellular domain of murine B7.1 were ampified by PCR from pLK444-mB7.1 (supplied by R. Germain NIH, USA) via primers that introduce 5' EcoRI and 3'Sma I sites-primers forward (SEQ ID NO: 9)

```
5' C TCG AAT TCC ACC ATG GCT TGC AAT TGT CAG TTG

ATG C 3'
```

reverse (SEQ ID NO: 10)

```
5' CTC CCC GGG CTT GCT ATC AGG AGG GTC TTC 3'
```

The B7.1 PCR product was cloned into pLINK via Eco RI and Sma I to form pBS/B7Link.

The $V_H$ and $V_L$ Of the 5T4 specific ScFv was amplified via primers-forward primer (SEQ ID NO: 11)

```
5' CTC ACT AGT GAG GTC CAG CTT CAG CAG TC 3'
```

reverse primer (SEQ ID NO: 12)

```
5' CTC GCG GCC GCT TAC CGT TTG ATT TCC AGC TTG

GTG CCT CCA CC 3'
```

That introduce 5' Spe I and 3' Not I sites from pHEN1-5T4 ScFv. PBS/B7Link was digested with Spe I and Not I and ligated with the ScFv to form OBM 233 consisting of the sequence shown as SEQ ID No. 5: B7 Link scFv sequence.

This fusion can be used to construct a recombinant vector e.g. retrovirus, Lentivirus, adenovirus, poxvirus, vaccina virus, baculovirus. Such vectors can be used to inject patient tumours directly. To deliver the fusion protein to tumour cells the recombinant vector is used to transduce macrophages/monocytes/CD34+ cells ex vivo before injection back into patients. These cells will traffic to tumours. The ScFv will bind to a specific tumour antigen expressed on the surface of tumour cells e.g. 5T4 (Myers et al 1994 JBC). B7 is found on the surface of professional antigen presenting cells e.g. macrophages, dendritic cells and B cells. It interacts with it ligands CD28 and CTL-A4 located on CD4 and CD8 cells. The simultaneous interaction of B7-CD28/CTL-A4 and MHC-peptide/T cell receptor leads to a pronounced increase in IL-2 which promotes CD8 (cytotoxic T cell) expansion (Linsley P S, Brady W, Grosmaire L, Aruffo A, Damle N K, Ledbetter J A J Exp Med 1991 Mar 1; 173 (3): 721-730 Binding of the B cell activation antigen B7 to CD28 costimulates T cell proliferation and I1-2 mRNA accumulation.) Tumour cells that have been B7 tranfected with B7 have been shown retardation in animal models (Townsend S E, Allison J P Science 1993 15; 259 (5093): 368-370).

Example 11

Transient Expression and Purification of B7-1/ScFv and LScFv

For transient expression of B7-1/ScFv the human CMV expression plasmid pCIneo (Promega) was used. B7/ScFv was excised from OBM 233 by digestion with EcoR I/Not I and cloned into pCIneo that was previously digested with EcoRI/Not I. Transient expression of recombinant protein is made by transfection of 293T cells with the relevant plasmid using calcium phosphate (Profectin, Promega). Conditions used were similar to those recommended by the manufacturer. To reduce bovine serum contamination serum free optimem media (Gibco BRL). After 36-48 hours transfection supernatants were harvested and spun through a Centriprep (Amicon, Glos. UK) 10 filter (all proteins larger than 10 kDa are purified/concentrated) and a Centricon (Amicon) 10 filter. Supernatants are concentrated approximately 30 fold.

For B7-1 to be biologically functional it must be able to display binding with one of it's natural ligands either CTLA-4 or CD28 found on the surface of specific populations of T cells (e.g CD4+). The biological activity B7-1/ScFv fusion protein was analysed for simultaneous interaction with its natural ligand CTLA-4 (in the form of CTLA4-Ig supplied by Ancell, Minn., USA) and A9 cells expressing human 5T4. Briefly: approximately $5\times10^5$ A9-h5T4 cells were incubated with 100 ul of either B7.1/ScFv or LScFv supernatant in a U bottom 96 well plate at 4° C. for 1 hour. After washing cells were incubated with CTLA4-Ig (Ancell) for 1 hour. After washing, bound CTLA4-Ig was detected using an FITC conjugated anti-mouse Ig (Dako).

Results show obvious binding of CTLA-Ig with the B7-1 extracellular domain, bound via the ScFv, to the surface of human 5T4 positive A9 cells. The lack of binding activity with 5T4 negative A9 cells further illustrates that the interaction of B7 with CTLA4-Ig and ScFv with 5T4 are specific.

Example 12

ScFv-IgG Fusion Example

Construction of ScFv-IgG

The sequence encoding a translation initiation sequence and the human immunoglobulin kappa light chain signal peptide is synthesised as two complementary single stranded oligonucleotides which when annealed also contain an internal Xho I site at the 5' end and in addition leave a Xba I compatible 5' overhang and a Pst I compatible 3' overhang (SEQ ID NO: 13)

```
ctagactcgagCCACC ATG GGA TGG AGC TGT ATC ATC CTC
TTC TTG GTA GCA ACA GCT ACA GGT GTC CAC TCC GAG
GTC CAG ctgca
```

and (SEQ ID NO: 14)

```
g CTG GAC CTC GGA GTG GAC ACC TGT AGC TGT TGC TAC
CAA GAA GAG GAT GAT ACA GCT CCA TCC CAT GGTGGctcg
agt
```

This is then cloned into pBluescript II (Stratagene) restricted with Xba I and Pst I to create pBSII/Leader.

The 5T4 scFv is amplified by PCR from pHEN1 using oligonucleotides which incorporate a Pst I site at the 5'end of the product and a Hind III at the 3'end

```
GTC CAG CTG CAG CAG TCT GG        (SEQ ID NO: 15)
```

and

```
CG TTT GAT TTC AAG CTT GGT GC     (SEQ ID NO: 16)
```

This is then restricted with those enzymes and inserted into pBSII/Leader restricted with the same enzymes, creating pBSII/Leader/scFv.

The HIgG1 constant region is amplified by PCR from the cloned gene using oligonucleotides which incorporate a Hind III site at the 5'end and a Xho I site at the 3' end (SEQ ID NO: 17)
gcgc AAG CTT gaa atc aaa cgg GCC TCC ACC AAG GGC CCA
and (SEQ ID NO: 19)
gcgc ctcgag TCA TTT ACC CGG AGA CAG GG This is then restricted with those enzymes and inserted into pBSII/Leader/scFv restricted with the same enzymes, creating pBSII/Leader/scFv/HG1. The sequence for this construct is shown in the Figures.

This fusion can be used to construct a recombinant vector e.g. retrovirus, Lentivirus, adenovirus, poxvirus, vaccinia virus, baculovirus. Such vectors can be used to inject patient tumours directly. To deliver the fusion protein to tumour cells the recombinant vector is used to transduce macrophages/monocytes/CD34+ cells ex vivo before injection back into patients. These cells will traffic to tumours. The ScFv will bind to a specific tumour antigen expressed on the surface of tumour cells e.g. 5T4 (Myers et al 1994 JBC). Bound IgG will promote specific tumour destruction via a collection of mechanisms collectively known as antibody dependent cellular cytotoxicity (Munn et al Can res 1991 ibid, Primus et al 1993 Cancer Res ibid).

Example 13

Construction of ScFv-IgEl (Human IgEl Heavy Constant Region)

A similar fusion construct of 5T4 scFv-human IgE constant heavy chain is made consisting of the sequence shown as SEQ ID No. 6.

This fusion construct is made by amplifying the human IgEl constant heavy region by PCR cDNA derived from human B-cells RNA by RT and subsequently using oligonucleotides which incorporate a Hind III site at the 5' end and a Xho I site at the 3'end (SEQ ID NO: 19)
gcgc AAG CTT gaa atc aaa cgg GCC TCC ACA CAG AGC CCA
and (SEQ ID NO: 20)
gcgc ctcgag TCA TTT ACC GGG ATT TAC AGA This is then restricted with those enzymes and inserted into pBSII/Leader/scFv restricted with the same enzymes, creating pBSII/Leader/scFv/HE1.

As described above the ScFv-IgE construct can be incorporated into a recombinant viral vector for use in gene therapy of cancer e.g. inject patient tissue directly or to transduce patient derived macrophages/moncytes/CD34+ cells ex vivo. The fusion protein will be secreted and will bind to tumour cells bearing the antigen that the ScFv is specific for. Binding of IgE to tumour cells should promote a strong histamine response via activation of mast cells. This will lead to a strong inflammatory response and destruction tumour cells as is reported for IgE cytotoxic destruction of parasites e.g. helminth larvae (Capron M 1988 Eosinophils in diseases: receptors and mediators. In progress in allergy and clinical immunology (Proc. 13$^{th}$ Int. Congress of Allergy and Clinical Immunology) Hogrefe & Huber Toronto p 6). Such inflammation and tumour destruction should initiate the recruitment of other immune effector cells. Past reports indicate that treatment with an MMTV antigen specific IgE Mab leads to protection from a tumour expressing MMTV antigen (Nagy E Istanvan B, Sehon A H 1991 Cancer Immunol. Immunotherapy vol 34: 63-69).

Example 14

Construction of B7/EGF

B7-EGF Synthetic Gene.

A fusion construct of B7-EGF is made by inserting a PCR product amplified from the region of the gene encoding the mature EGF peptide (see accession number X04571) into pBS/B7 Link. This construct has the sequence shown as SEQ ID No. 7.

Using cDNA derived by RT of RNA isolated from a cell line such the 293 human kidney line (ATCC: CRL1573), the DNA is amplified by PCR using oligonucleotides containing a Spe I restriction enzyme site at the N-terminus and a stop codon and a Not I site at the C-terminus (SEQ ID NO: 21)
GG ACT AGT AAT AGT GAC TCT GAA TGT CCC
and (SEQ ID NO: 22)
ATT AGC GGC CGC TTA GCG CAG TTC CCA CCA CTT C The resulting product is digested with those enzymes and ligated to pBS/B7 Link which has been restricted with the same enzymes creating pBS/B7 Link EGF. The B7 Link EGF cassette is then excised with Eco RI and Not I and inserted into a derivative of pHIT111 (Soneoka et al, 1995, Nucl Acid Res 23; 628) which no longer carries the LacZ gene.

An alternative to using ScfV is to use growth factors that have a high affinity to their corresponding receptor e.g. epidermal growth factor which binds to several receptors including erb-2 which is highly associated with tumourgenesis.

As described above the fusion construct can be incorporated into a recombinant viral vector for use in gene therapy e.g. inject patient tissue directly or to transduce patient derived macrophages/moncytes/CD34+ cells ex vivo. The fusion protein will be secreted and will bind to tumour cells bearing the erb-2 antigen.

Epidermal growth factor (EGF) will bind to its ligand erb-2 (an EGF receptor) thus obviating the requirement of a ScFv. Erb-2 is highly associated with tumour cells (Hynes N E Semin Cancer Biol 1993 Feb. ; 4 (1): 19-26, Amplification and over expression of the erbB-2 gene in human tumors: its involvement in tumor development, significance as a pronostic factor, and potential as a target for cancer therapy). B7 is found on the surface of professional antigen presenting cells e.g. macrophages, dendritic cells and B cells. It interacts with it ligands CD28 and CTL-A4 located on CD4 and CD8 cells. The simultaneous interaction of B7-CD28/CTL-A4 and MHC-peptide/T cell receptor leads to massive increase in IL-2 which promotes CD8 (cytotoxic T cell) expansion (Linsley P S, Brady W, Grosmaire L, Aruffo A, Damle N K, Ledbetter J A J Exp Med 1991 Mar. 1 ; 173 (3): 721-730 Binding of the B cell activation antigen B7 to CD28 costimulates T cell proliferation and interleukin 2 mRNA accumulation.) Tumour cells that have been B7 transfected with B7 have shown retardation in animal models (Townsend S E, Allison J P Science 1993 15; 259 (5093): 368-370 Tumor rejection after direct costimulation of CD8+ T cells by B7-transfected melanoma cells). It is has been reported that B7 will enhance the CTL response to tumour antigens specific to tumour cells thus leading to the destruction of all such cells.

Example 15

Production of Cell Lines Expressing Fusion Constructs

The ScFv-IgG gene was excised from pBSII/L/ScFv/hIgG1 by Xho I digestion, and cloned into pLXSN via the Xho I site, to make pLXSN/ScFv-IgG, such that after chromosomal integration it is under transcriptional control of the LTR. Virus was made in the human kidney cell line 293T by co-transfecting plasmids containing the MLV gap-pol genes (pCIEGPPD) and the VSV G envelope (pRV67) using the triple plasmid HIT system (Landau & Littman 1992 J Virol 66 5110, Soneoka Y et al 1995 NAR 23: 628-633). Virus is harvested after 48 hours and used to transduce BHK-21 cells (ATCC#CCL-10). Approximately 24 hours post-transduction, transduced cells are selected by the addition of 1 mg/ml G418 (Gibco BRL) to culture medium. The supernatant from positive colonies was harvested and concentrated by centrifugation through a Centriprep (Amicon, Glos. UK) 10 filter (all proteins larger than 10 kDa are purified/concentrated) and a Centricon (Amicon) 10 filter. Supernatants were concentrated approximately 30 fold.

Other fusion proteins are cloned into pLXSN via the Xho I site and expressed and concentrated using a similar protocol.

FACS analysis of fusion protein binding with cells expressing specific ligand To determine if the ScFv-IgG fusion protein is specific for its antigen, human 5T4, FACS analysis of a human bladder carcinoma tumour line (EJ) or a stable murine cell line expressing h5T4, A9-h5T4 (Myers et al 1994 JBC) and a 5T4 negative line A9-neo was carried out. Approximately $5\times10^5$ A9 or EJ cells, in a round bottom 96 well plate (Falcon) were incubated with 100 ul of a 1:5 dilution of concentrated supernatant (as described above) for 1 hour at 4° C. After washing, bound protein is detected using an anti human IgG/FITC conjugated antibody (Dako). Cells were analysed on a Becton Dickinson FACS machine. FACS results show that there is at least a 1 log shift in fluorescence activity in those 5T4 positive cells treated with the ScFv-IgG construct compared to the negative control construct consisting of the ScFv protein alone. A9 neo FACS shows that there is no non-specific binding of the ScFv component of the fusion protein.

FACS analysis of ScFv-IgE is carried out similar to above except that anti-human IgE-FITC (Dako) is used to detect binding of the fusion protein.

The B7/EGF fusion protein is analysed for binding using FACS and HC11-erb-2 positive cells (Hynes et al 1990). CTLA4-Ig (Ancell, USA) is used to analyse the bioactivity of the B7 component of the bound fusion protein. Anti-mouse IgG-FITC is used to show CTLA- 4 binding.

SUMMARY

The present invention therefore provides a means for delivering, for example, therapeutic compounds to a tumour site.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A vector comprising a nucleotide sequence coding for a protein consisting essentially of an antibody that binds 5T4, said antibody comprising 5T4 complementarity determining regions (CDRs) of the 5T4 ScFv antibody amino acid sequence encoded by SEQ ID NO:1 or CDRs of the 5T4 Sab antibody amino acid sequence encoded by SEQ ID NO:2.

2. The vector according to claim 1, wherein the antibody is a 5T4 Fab, 5T4 Fv or 5T4 scFc fragment.

3. The vector according to claim 1, wherein the antibody is a humanized antibody.

4. A vector comprising a nucleotide sequence coding for a protein consisting essentially of an antibody that binds 5T4, said antibody comprising 5T4 complementarity determining regions (CDRs) having the amino acid sequence of KASQSVSNDVA (SEQ ID NO:26), YTSSRYA (SEQ ID NO:27), QQDYNSPPT (SEQ ID NO:28), GYYMH (SEQ ID NO:29), RINPNNGVTLYNQKFKD (SEQ ID NO:30), and STMITNYVMDY (SEQ ID NO:31).

5. The vector according to claim 4, wherein the antibody is a 5T4 Fab, 5T4 Fv or 5T4 scFc fragment.

6. The vector according to claim 4, wherein the antibody is a humanized antibody.

* * * * *

SEQUENCE LISTING

```
<160> NUMBER OF SEQ ID NOS: 31

<210> SEQ ID NO 1
<211> LENGTH: 910
<212> TYPE: DNA
<213> ORGANISM: Artificial Sequence
<220> FEATURE:
<223> OTHER INFORMATION: Coding sequence of a 5T4scFv designated
      5T4scFv.1
<220> FEATURE:
<221> NAME/KEY: misc_feature
<222> LOCATION: (1)..(910)
<223> OTHER INFORMATION: n = a,t,c or g

<400> SEQUENCE: 1

gaggtccagc ttcagcagtc tggacctgac ctggtgaagc ctggggcttc vsgdvkgasa     60

gtgaagatat cctgcaaggc ttctggttac tcattcactg gctactacav ksckasgyst    120

gyytgcactg ggtgaagcag agccatggaa agagccttga gtggattgga cgtmhwvksh    180

gkswgratta atcctaacaa tggtgttact ctctacaacc agaaattcaa ggacaannng    240

vtynkkdkgg ccatattaac tgtagacaag tcatccacca cagcctacat ggagctccat    300

vdkssttaym gcagcctgac atctgaggac tctgcggtct attactgtgc aagatctact    360

rstsdsavyy carstatgat tacgaactat gttatggact actggggtca agtaacctca    420

gtcacmtnyv mdywgvtsvt cgtctcctca ggtggtggtg ggagcggtgg tggcggcact    480
```

```
ggcggcggcg vssggggsgg ggtggggatc tagtattgtg atgacccaga ctcccacatt    540

cctgcttgtt tcagcagssv mtttvsagga gacagggtta ccataacctg caaggccagt    600

cagagtgtga gtaatgagdr vttckassvs ndtgtagdtt ggtaccaaca gaagccaggg    660

cagtctccta cactgctcat atvawykgst cctatacatc cagtcgctac gctggagtcc    720

ctgatcgctt cattggcagt sytssryagv drgsggatat gggacggatt tcactttcac    780

catcagcact ttgcaggctg aagagygtdt tstadcctgg cagtttattt ctgtcagcaa    840

gattataatt ctcctccgac gttcgavycd ynstgtggag gcaccaagct ggaaatcaaa    900

cgggggtkkr                                                           910
```

<210> SEQ ID NO 2
<211> LENGTH: 2239
<212> TYPE: DNA
<213> ORGANISM: Artificial Sequence
<220> FEATURE:
<223> OTHER INFORMATION: Coding sequence of a 5T4scFv designated 5T4scFv1
<220> FEATURE:
<221> NAME/KEY: misc_feature
<222> LOCATION: (1)..(2239)
<223> OTHER INFORMATION: n = a,t,c or g

<400> SEQUENCE: 2

```
aagcttccac catgggatgg agctgtatca tcctcttctt ggtagcaaca astmgwscva     60

tgctacaggt gtccactccg aggtccagct tcagcagtct ggacctgacc tatgvhsvsg    120

dggtgaagcc tggggcttca gtgaagatat cctgcaaggc ttctggttac tvkgasvksc    180

kasgycattc actggctact acatgcactg ggtgaagcag agccatggaa agagcstgyy    240

mhwvkshgks cttgagtgga ttggacgtat taatcctaac aatggtgtta ctctctacaa    300

wgrnnngvty nccagaaatt caaggacaag gccatattaa ctgtagacaa gtcatccacc    360

akkdkatvdk sstcagccta catggagctc cgcagcctga catctgagga ctctgcggtc    420

tattaymrst sdsavytact gtgcaagatc tactatgatt acgaactatg ttatggacta    480

ctggggycar stmtnyvmdy wgtcaagtaa cctcagtcac cgtctcctca ggtggtggtg    540

ggagcggtgg tgvtsvtvss ggggsgggcg gcactggcgg cggcggatct agtattgtga    600

tgacccagac tcccacaggt ggggssvmtt tttcctgctt gtttcagcag gagacagggt    660

taccataacc tgcaaggcca gvsagdrvtt ckastcagag tgtgagtaat gatgtagctt    720

ggtaccaaca gaagccaggg cagtsvsndv awykgctcct acactgctca tatcctatac    780

atccagtcgc tacgctggag tccctstsyt ssryagvgat cgcttcattg gcagtggata    840

tgggacggat ttcactttca ccatcagdrg sgygtdttsc actttgcagg ctgaagacct    900

ggcagtttat ttctgtcagc aagattatat adavycdyat tctcctccga cgttcggtgg    960

aggcaccaag ctggaaatca aacgggccns tgggtkkrat ccaccaaggg cccatcggtc   1020

ttcccccctgg caccctcctc caagagcacs tkgsvassks tctctggggg cacagcggcc  1080

ctgggctgcc tggtcaagga ctacttcccc gsggtaagcv kdyaaccggt gacggtgtcg   1140

tggaactcag gcgccctgac cagcggcgtg cacvtvswns gatsgvhacc ttcccggctg   1200

tcctacagtc ctcaggactc tactccctca gcagcgttav ssgysssvgg tgaccgtgcc   1260

ctccagcagc ttgggcaccc agacctacat ctgcaacgvt vsssgttycn tgaatcacaa   1320

gcccagcaac accaaggtgg acaagaaagt tgagcccaaa vnhksntkvd kkvktcttgt   1380

gacaaaactc acacatgccc accgtgccca gcacctgaac tcctscdkth tccagggggg   1440
```

```
accgtcagtc ttcctcttcc ccccaaaacc caaggacacc ctcaggsvkk dttgatctcc   1500

cggacccctg aggtcacatg cgtggtggtg gacgtgagcc acmsrtvtcv vvdvshgaag   1560

accctgaggt caagttcaac tggtacgtgg acggcgtgga ggtgcadvkn wyvdgvvhta   1620

atgccaagac aaagccgcgg gaggagcagt acaacagcac gtaccgtgna ktkrynstyr   1680

tggtcagcgt cctcaccgtc ctgcaccagg actggctgaa tggcaaggag vvsvtvhdwn   1740

gktacaagtg caaggtctcc aacaaagccc tcccagcccc catcgagaaa acykckvsnk   1800

aaktcatctc caaagccaaa gggcagcccc gagaaccaca ggtgtacacc ctgcskakgr   1860

vytccccatc ccgggatgag ctgaccaaga accaggtcag cctgacctgc ctgsrdtknv   1920

stcgtcaaag gcttctatcc cagcgacatc gccgtggagt gggagagcaa tggvkgysda   1980

vwsnggcagc cggagaacaa ctacaagacc acgcctcccg tgctggactc cgacgnnykt   2040

tvdsdgctcc ttcttcctct acagcaagct caccgtggac aagagcaggt ggcaggsysk   2100

tvdksrwcag ggaacgtctt ctcatgctcc gtgatgcat gaggctctgc acaaccagnv   2160

scsvmhahnh ctacacgcag aagagcctct ccctgtctcc gggtaaatga gtgcgacggc   2220

ytksssgkvr rcaagctts                                                2239


<210> SEQ ID NO 3
<211> LENGTH: 1809
<212> TYPE: DNA
<213> ORGANISM: Artificial Sequence
<220> FEATURE:
<223> OTHER INFORMATION: Coding sequence of B7-1.5T4.1
<220> FEATURE:
<221> NAME/KEY: misc_feature
<222> LOCATION: (1)..(1809)
<223> OTHER INFORMATION: n = a,t,c or g

<400> SEQUENCE: 3

atgggccaca cacggaggca gggaacatca ccatccaagt gtccatacct mghtrrgtss     60

kcycaatttc tttcagctct tggtgctggc tggtctttct cacttctgtt cagnvagshc    120

sgtgttatcc acgtgaccaa ggaagtgaaa gaagtggcaa cgctgtcctg tgvhvtkvkv    180

atscggtcac aatgtttctg ttgaagagct ggcacaaact cgcatctact ggcaghnvsv    240

atrywaaagg agaagaaaat ggtgctgact atgatgtctg ggacatgaa tatatkkkmv     300

tmmsgdmngg cccgagtaca agaaccggac catctttgat atcactaata acctctccwy    360

knrtdtnnsa ttgtgatcct ggctctgcgc ccatctgacg agggcacata cgagtgtgtv    420

arsdgtycvt gttctgaagt atgaaaaaga cgctttcaag cgggaacacc tggctgaagv    480

kykdakrhat gacgttatca gtcaaagctg acttccctac acctagtata tctgactttv    540

tsvkadtssd gaaattccaa cttctaatat tagaaggata atttgctcaa cctctggagg    600

tsnrrcstsg gttttccaga gcctcacctc tcctggttgg aaaatggaga agaattaaat    660

ghswngncca tcaacacaac agtttcccaa gatcctgaaa ctgagctcta tgctgttant    720

tvsdtyavag cagcaaactg gatttcaata tgacaaccaa ccacagcttc atgtgtctss    780

kdnmttnhsm ccatcaagta tggacattta agagtgaatc agaccttcaa ctggaataca    840

akyghrvntn wntccaagca agagcatttt cctgatggag gcgggggatc cgaggtccag    900

ctttkhdggg gsvcagcagt ctggacctga cctggtgaag cctggggctt cagtgaagat    960

atcsgdvkga svksctgcaa ggcttctggt tactcattca ctggctacta catgcactgg   1020

gtgackasgy stgyymhwva gcagagccat ggaaagagcc ttgagtggat tggacgtatt   1080

aatcctaack shgkswgrnn aatggtgtta ctctctacaa ccagaaattc aaggacaagg   1140
```

```
ccatattaac ngvtynkkdk attgtagaca agtcatccac cacagcctac atggagctcc   1200

gcagcctgac atvdksstta ymrstctgag gactctgcgg tctattactg tgcaagatct   1260

actatgatta cgaacsdsav yycarstmtn tatgttatgg actactgggg tcaagtaacc   1320

tcagtcaccg tctcctcagg yvmdywgvts vtvssgtggt ggtgggagcg gtggtggcgg   1380

cactggcggc ggcggatcta gtattggggs ggggtggggs stgatgaccc agactcccac   1440

attcctgctt gtttcagcag gagacagggt tvmtttvsag drvaccataa cctgcaaggc   1500

cagtcagagt gtgagtaatg atgtagcttg gtattckass vsndvawycc aacagaagcc   1560

agggcagtct cctacactgc tcatatccta tacatccakg stsytsgtcg ctacgctgga   1620

gtccctgatc gcttcattgg cagtggatat gggacgsrya gvdrgsgygt gatttcactt   1680

tcaccatcag cactttgcag gctgaagacc tggcagttta dttstadavy tttctgtcag   1740

caagattata attctcctcc gacgttcggt ggaggcacca cdynstgggt agctggaaat   1800

caaataakk                                                           1809
```

<210> SEQ ID NO 4
<211> LENGTH: 887
<212> TYPE: DNA
<213> ORGANISM: Artificial Sequence
<220> FEATURE:
<223> OTHER INFORMATION: Human B7-2 sequence followed by a linker
<220> FEATURE:
<221> NAME/KEY: misc_feature
<222> LOCATION: (1)..(887)
<223> OTHER INFORMATION: n = a,t,c or g

<400> SEQUENCE: 4

```
atgggactga gtaacattct ctttgtgatg gccttcctgc tctctggtgc mgsnvmasga     60

tgctcctctg aagattcaag cttatttcaa tgagactgca gacctgccat akayntadgc    120

caatttgcaa actctcaaaa ccaaagcctg agtgagctag tagtatttca nsnssvvtgg    180

caggaccagg aaaacttggt tctgaatgag gtatacttag gcaaagawdn vnvygkgaaa    240

tttgacagtg ttcattccaa gtatatgggc cgcacaagtt ttgattkdsv hskymgrtsd    300

cggacagttg gaccctgaga cttcacaatc ttcagatcaa ggacaagggc sdswtrhnkd    360

kgttgtatca atgtatcatc catcacaaaa agcccacagg aatgattcgc atychhkktg    420

mrccaccaga tgaattctga actgtcagtg cttgctaact tcagtcaacc tghmnssvan    480

saaatagtac caatttctaa tataacagaa aatgtgtaca taaatttgac cvsntnvynt    540

tgctcatcta tacacggtta cccagaacct aagaagatga gtgttttgct csshgykkms    600

vaagaaccaa gaattcaact atcgagtatg atggtattat gcagaaatct crtknstydg    660

mksaagataa tgtcacagaa ctgtacgacg tttccatcag cttgtctgtt tcadnvtydv    720

sssvsttccc tgatgttacg agcaatatga ccatcttctg tattctggaa actgadvtsn    780

mtctdcaaga cgcggctttt atcttcacct ttctctatag agcttgagga ccctcktrss    840

sdagcctccc ccagaccaca ttcctggagg cgggggatcc dhggggs                  887
```

<210> SEQ ID NO 5
<211> LENGTH: 1518
<212> TYPE: DNA
<213> ORGANISM: Artificial Sequence
<220> FEATURE:
<223> OTHER INFORMATION: pBSII/Leader/scFv/HG1

<400> SEQUENCE: 5

```
atggcttgca attgtcagtt gatgcaggat acaccactcc tcaagtttcc atgtccaagg     60
```

```
ctcattcttc tctttgtgct gctgattcgt ctttcacaag tgtcttcaga tgttgatgaa    120

caactgtcca agtcagtgaa agataaggta ttgctgcctt gccgttacaa ctctccgcat    180

gaagatgagt ctgaagaccg aatctactgg caaaaacatg acaaagtggt gctgtctgtc    240

attgctggga aactaaaagt gtggcccgag tataagaacc ggactttata tgacaacact    300

acctactctc ttatcatcct gggcctggtc ctttcagacc ggggcacata cagctgtgtc    360

gttcaaaaga aggaaagagg aacgtatgaa gttaaacact tggctttagt aaagttgtcc    420

atcaaagctg acttctctac ccccaacata actgagtctg gaaacccatc tgcagacact    480

aaaaggatta cctgctttgc ttccgggggt ttcccaaagc ctcgcttctc ttggttggaa    540

aatggaagag aattacctgg catcaatacg acaatttccc aggatcctga atctgaattg    600

tacaccatta gtagccaact agatttcaat acgactcgca accacaccat taagtgtctc    660

attaaatatg gagatgctca cgtgtcagag gacttcacct gggaaaaacc cccagaagac    720

cctcctgata gcaagcccgg gggtggtggg agcggtggtg gcggcagtgg cggcggcgga    780

actagtgagg tccagcttca gcagtctgga cctgacctgg tgaagcctgg ggcttcagtg    840

aagatatcct gcaaggcttc tggttactca ttcactggct actacatgca ctgggtgaag    900

cagagccatg gaaagagcct tgagtggatt ggacgtatta atcctaacaa tggtgttact    960

ctctacaacc agaaattcaa ggacaaggcc atattaactg tagacaagtc atccaccaca   1020

gcctacatgg agctccgcag cctgacatct gaggactctg cggtctatta ctgtgcaaga   1080

tctactatga ttacgaacta tgttatggac tactggggtc aagtaacttc agtcaccgtc   1140

tcttcaggtg gtggtgggag cggtggtggc ggcactggcg gcggcggatc tagtattgtg   1200

atgacccaga ctcccacatt cctgcttgtt tcagcaggag acagggttac cataacctgc   1260

aaggccagtc agagtgtgag taatgatgta gcttggtacc aacagaagcc agggcagtct   1320

cctacactgc tcatatccta tacatccagt cgctacgctg gagtccctga tcgcttcatt   1380

ggcagtggat atgggacgga tttcactttc accatcagca ctttgcaggc tgaagacctg   1440

gcagtttatt tctgtcagca agattataat tctcctccga cgttcggtgg aggcaccaag   1500

ctggaaatca aacggtaa                                                 1518
```

<210> SEQ ID NO 6
<211> LENGTH: 2090
<212> TYPE: DNA
<213> ORGANISM: Artificial Sequence
<220> FEATURE:
<223> OTHER INFORMATION: 5T4 scFv-human IgE fusion construct

<400> SEQUENCE: 6

```
ctcgagccac catgggatgg agctgtatca tcctcttctt ggtagcaaca gctacaggtg     60

tccactccga ggtccagctg cagcagtctg gacctgacct ggtgaagcct ggggcttcag    120

tgaagatatc ctgcaaggct tctggttact cattcactgg ctactacatg cactgggtga    180

agcagagcca tggaaagagc cttgagtgga ttggacgtat taatcctaac aatggtgtta    240

ctctctacaa ccagaaattc aaggacaagg ccatattaac tgtagacaag tcatccacca    300

cagcctacat ggagctccgc agcctgacat ctgaggactc tgcggtctat tactgtgcaa    360

gatctactat gattacgaac tatgttatgg actactgggg tcaagtaact tcagtcaccg    420

tctcttcagg tggtggtggg agcggtggtg gcggcactgg cggcggcgga tctagtattg    480

tgatgaccca gactcccaca ttcctgcttg tttcagcagg agacagggtt accataacct    540

gcaaggccag tcagagtgtg agtaatgatg tagcttggta ccaacagaag ccagggcagt    600
```

```
ctcctacact gctcatatcc tatacatcca gtcgctacgc tggagtccct gatcgcttca    660

ttggcagtgg atatgggacg gatttcactt tcaccatcag cactttgcag gctgaagacc    720

tggcagttta tttctgtcag caagattata attctcctcc gacgttcggt ggaggcacca    780

agcttgaaat caaacgggcc tccacacaga gcccatccgt cttccccttg acccgctgct    840

gcaaaaacat tccctccaat gccacctccg tgactctggg ctgcctggcc acgggctact    900

tcccggagcc ggtgatggtg acctgggaca caggctccct caacgggaca actatgacct    960

taccagccac caccctcacg ctctctggtc actatgccac catcagcttg ctgaccgtct   1020

cgggtgcgtg ggccaagcag atgttcacct gccgtgtggc acacactcca tcgtccacag   1080

actgggtcga caacaaaacc ttcagcgtct gctccaggga cttcaccccg cccaccgtga   1140

agatcttaca gtcgtcctgc gacggcggcg ggcacttccc cccgaccatc cagctcctgt   1200

gcctcgtctc tgggtacacc ccagggacta tcaacatcac ctggctggag gacgggcagg   1260

tcatggacgt ggacttgtcc accgcctcta ccacgcagga gggtgagctg gcctccacac   1320

aaagcgagct caccctcagc cagaagcact ggctgtcaga ccgcacctac acctgccagg   1380

tcacctatca aggtcacacc tttgaggaca gcaccaagaa gtgtgcagat tccaacccga   1440

gaggggtgag cgcctaccta agccggccca gcccgttcga cctgttcatc cgcaagtcgc   1500

ccacgatcac ctgtctggtg gtggacctgg cacccagcaa ggggaccgtg aacctgacct   1560

ggtcccgggc cagtgggaag cctgtgaacc actccaccag aaaggaggag aagcagcgca   1620

atggcacgtt aaccgtcacg tccaccctgc cggtgggcac ccgagactgg atcgaggggg   1680

agacctacca gtgcagggtg acccaccccc acctgcccag ggccctcatg cggtccacga   1740

ccaagaccag cggcccgcgt gctgccccgg aagtctatgc gtttgcgacg ccggagtggc   1800

cggggagccg ggacaagcgc accctcgcct gcctgatcca gaacttcatg cctgaggaca   1860

tctcggtgca gtggctgcac aacgaggtgc agctcccgga cgcccggcac agcacgacgc   1920

agccccgcaa gaccaagggc tccggcttct tcgtcttcag ccgcctggag gtgaccaggg   1980

ccgaatggga gcagaaagat gagttcatct gccgtgcagt ccatgaggca gcgagcccct   2040

cacagaccgt ccagcgagcg gtgtctgtaa atcccggtaa atgagagctc              2090
```

<210> SEQ ID NO 7
<211> LENGTH: 945
<212> TYPE: DNA
<213> ORGANISM: Artificial Sequence
<220> FEATURE:
<223> OTHER INFORMATION: B7-EGF fusion construct

<400> SEQUENCE: 7

```
atggcttgca attgtcagtt gatgcaggat acaccactcc tcaagtttcc atgtccaagg     60

ctcattcttc tctttgtgct gctgattcgt ctttcacaag tgtcttcaga tgttgatgaa    120

caactgtcca agtcagtgaa agataaggta ttgctgcctt gccgttacaa ctctccgcat    180

gaagatgagt ctgaagaccg aatctactgg caaaaacatg acaaagtggt gctgtctgtc    240

attgctggga aactaaaagt gtggcccgag tataagaacc ggactttata tgacaacact    300

acctactctc ttatcatcct gggcctggtc ctttcagacc ggggcacata cagctgtgtc    360

gttcaaaaga aggaaagagg aacgtatgaa gttaaacact tggctttagt aaagttgtcc    420

atcaaagctg acttctctac ccccaacata actgagtctg gaaacccatc tgcagacact    480

aaaaggatta cctgctttgc ttccgggggt ttcccaaagc ctcgcttctc ttggttggaa    540

aatggaagag aattacctgg catcaatacg acaatttccc aggatcctga atctgaattg    600
```

```
tacaccatta gtagccaact agatttcaat acgactcgca accacaccat taagtgtctc    660

attaaatatg gagatgctca cgtgtcagag gacttcacct gggaaaaacc cccagaagac    720

cctcctgata gcaagcccgg gggtggtggg agcggtggtg gcggcagtgg cggcggcgga    780

actagtaata gtgactctga atgtcccctg tcccacgatg ggtactgcct ccatgatggt    840

gtgtgcatgt atattgaagc attggacaag tatgcatgca actgtgttgt tggctacatc    900

ggggagcgat gtcagtaccg agacctgaag tggtgggaac tgcgc                    945


<210> SEQ ID NO 8
<211> LENGTH: 47
<212> TYPE: DNA
<213> ORGANISM: Artificial Sequence
<220> FEATURE:
<223> OTHER INFORMATION: Oligonucleotide

<400> SEQUENCE: 8

ctagttccgc cgccgccact gccgccacca ccgctcccac caccccc                  47


<210> SEQ ID NO 9
<211> LENGTH: 38
<212> TYPE: DNA
<213> ORGANISM: Artificial Sequence
<220> FEATURE:
<223> OTHER INFORMATION: Forward primer

<400> SEQUENCE: 9

ctcgaattcc accatggctt gcaattgtca gttgatgc                            38


<210> SEQ ID NO 10
<211> LENGTH: 30
<212> TYPE: DNA
<213> ORGANISM: Artificial Sequence
<220> FEATURE:
<223> OTHER INFORMATION: Reverse primer

<400> SEQUENCE: 10

ctccccgggc ttgctatcag gagggtcttc                                     30


<210> SEQ ID NO 11
<211> LENGTH: 29
<212> TYPE: DNA
<213> ORGANISM: Artificial Sequence
<220> FEATURE:
<223> OTHER INFORMATION: Forward primer

<400> SEQUENCE: 11

ctcactagtg aggtccagct tcagcagtc                                      29


<210> SEQ ID NO 12
<211> LENGTH: 44
<212> TYPE: DNA
<213> ORGANISM: Artificial Sequence
<220> FEATURE:
<223> OTHER INFORMATION: Reverse primer

<400> SEQUENCE: 12

ctcgcggccg cttaccgttt gatttccagc ttggtgcctc cacc                     44


<210> SEQ ID NO 13
<211> LENGTH: 87
<212> TYPE: DNA
<213> ORGANISM: Artificial Sequence
<220> FEATURE:
<223> OTHER INFORMATION: Oligonucleotide containing translation
      initiation site and signal peptide
```

<400> SEQUENCE: 13
ctagactcga gccaccatgg gatggagctg tatcatcctc ttcttggtag caacagctac 60
aggtgtccac tccgaggtcc agctgca 87

<210> SEQ ID NO 14
<211> LENGTH: 79
<212> TYPE: DNA
<213> ORGANISM: Artificial Sequence
<220> FEATURE:
<223> OTHER INFORMATION: Oligonucleotide containing translation initiation site and signal peptide

<400> SEQUENCE: 14
gctggacctc ggagtggaca cctgtagctg ttgctaccaa gaagaggatg atacagctcc 60
atcccatggt ggctcgagt 79

<210> SEQ ID NO 15
<211> LENGTH: 20
<212> TYPE: DNA
<213> ORGANISM: Artificial Sequence
<220> FEATURE:
<223> OTHER INFORMATION: Primer with PstI site

<400> SEQUENCE: 15
gtccagctgc agcagtctgg 20

<210> SEQ ID NO 16
<211> LENGTH: 22
<212> TYPE: DNA
<213> ORGANISM: Artificial Sequence
<220> FEATURE:
<223> OTHER INFORMATION: Primer with Hind III site

<400> SEQUENCE: 16
cgtttgattt caagcttggt gc 22

<210> SEQ ID NO 17
<211> LENGTH: 40
<212> TYPE: DNA
<213> ORGANISM: Artificial Sequence
<220> FEATURE:
<223> OTHER INFORMATION: Primer for the constant region which incorporates a Hind III site

<400> SEQUENCE: 17
gcgcaagctt gaaatcaaac gggcctccac caagggccca 40

<210> SEQ ID NO 18
<211> LENGTH: 30
<212> TYPE: DNA
<213> ORGANISM: Artificial Sequence
<220> FEATURE:
<223> OTHER INFORMATION: Primer for the constant region which incorporates a XhoI site

<400> SEQUENCE: 18
gcgcctcgag tcatttaccc ggagacaggg 30

<210> SEQ ID NO 19
<211> LENGTH: 40
<212> TYPE: DNA
<213> ORGANISM: Artificial Sequence
<220> FEATURE:
<223> OTHER INFORMATION: Oligonucleotide with Hind III site

<400> SEQUENCE: 19
gcgcaagctt gaaatcaaac gggcctccac acagagccca 40

<210> SEQ ID NO 20
<211> LENGTH: 31
<212> TYPE: DNA
<213> ORGANISM: Artificial Sequence
<220> FEATURE:
<223> OTHER INFORMATION: Oligonucleotide with XhoI site

<400> SEQUENCE: 20
gcgcctcgag tcatttaccg ggatttacag a 31

<210> SEQ ID NO 21
<211> LENGTH: 29
<212> TYPE: DNA
<213> ORGANISM: Artificial Sequence
<220> FEATURE:
<223> OTHER INFORMATION: Oligonucleotide with SpeI site

<400> SEQUENCE: 21
ggactagtaa tagtgactct gaatgtccc 29

<210> SEQ ID NO 22
<211> LENGTH: 34
<212> TYPE: DNA
<213> ORGANISM: Artificial Sequence
<220> FEATURE:
<223> OTHER INFORMATION: Oligonucleotide with NotI site and Stop codon

<400> SEQUENCE: 22
attagcggcc gcttagcgca gttcccacca cttc 34

<210> SEQ ID NO 23
<211> LENGTH: 68
<212> TYPE: DNA
<213> ORGANISM: Artificial Sequence
<220> FEATURE:
<223> OTHER INFORMATION: Translation initiation and secretion signal

<400> SEQUENCE: 23
aagcttccac catgggatgg agctgtatca tcctcttctt ggtagcaaca gctacaggtg 60
tccactcc 68

<210> SEQ ID NO 24
<211> LENGTH: 43
<212> TYPE: DNA
<213> ORGANISM: Artificial Sequence
<220> FEATURE:
<223> OTHER INFORMATION: Coding sequence of a 5T4scFv designated 5T4scFv.1

<400> SEQUENCE: 24
gggggtggtg ggagcggtgg tggcggcagt ggcggcggcg gaa 43

<210> SEQ ID NO 25
<211> LENGTH: 5
<212> TYPE: PRT
<213> ORGANISM: Artificial Sequence
<220> FEATURE:
<223> OTHER INFORMATION: flexible linker

<400> SEQUENCE: 25

Gly Gly Gly Gly Ser
1 5

<210> SEQ ID NO 26
<211> LENGTH: 11
<212> TYPE: PRT
<213> ORGANISM: Artificial Sequence
<220> FEATURE:
<223> OTHER INFORMATION: CDR of the 5T4 antibody

<400> SEQUENCE: 26

Lys Ala Ser Gln Ser Val Ser Asn Asp Val Ala
1               5                   10

<210> SEQ ID NO 27
<211> LENGTH: 7
<212> TYPE: PRT
<213> ORGANISM: Artificial Sequence
<220> FEATURE:
<223> OTHER INFORMATION: CDR of the 5T4 antibody

<400> SEQUENCE: 27

Tyr Thr Ser Ser Arg Tyr Ala
1               5

<210> SEQ ID NO 28
<211> LENGTH: 9
<212> TYPE: PRT
<213> ORGANISM: Artificial Sequence
<220> FEATURE:
<223> OTHER INFORMATION: CDR of the 5T4 antibody

<400> SEQUENCE: 28

Gln Gln Asp Tyr Asn Ser Pro Pro Thr
1               5

<210> SEQ ID NO 29
<211> LENGTH: 5
<212> TYPE: PRT
<213> ORGANISM: Artificial Sequence
<220> FEATURE:
<223> OTHER INFORMATION: CDR of the 5T4 antibody

<400> SEQUENCE: 29

Gly Tyr Tyr Met His
1               5

<210> SEQ ID NO 30
<211> LENGTH: 17
<212> TYPE: PRT
<213> ORGANISM: Artificial Sequence
<220> FEATURE:
<223> OTHER INFORMATION: CDR of the 5T4 antibody

<400> SEQUENCE: 30

Arg Ile Asn Pro Asn Asn Gly Val Thr Leu Tyr Asn Gln Lys Phe Lys
1               5                   10                  15

Asp

<210> SEQ ID NO 31
<211> LENGTH: 11
<212> TYPE: PRT
<213> ORGANISM: Artificial Sequence
<220> FEATURE:
<223> OTHER INFORMATION: CDR of the 5T4 antibody

<400> SEQUENCE: 31

Ser Thr Met Ile Thr Asn Tyr Val Met Asp Tyr
1               5                   10